United States Patent [19]

Pfiffner

[11] 4,241,058
[45] Dec. 23, 1980

[54] HETEROCYCLICS USEFUL AS FUNGICIDES AND FUNGICIDAL COMPOSITIONS THEREOF

[75] Inventor: Albert Pfiffner, Bülach, Switzerland

[73] Assignee: Hoffmann-La Roche Inc., Nutley, N.J.

[21] Appl. No.: 853,018

[22] Filed: Nov. 18, 1977

[30] Foreign Application Priority Data

Nov. 22, 1976 [AT] Austria .................................. 8660/76

[51] Int. Cl.³ ................. C07D 295/02; A61K 31/535; A01N 43/84; C07D 295/22
[52] U.S. Cl. ................................. 424/248.4; 424/258; 424/267; 544/105; 544/173; 544/178; 546/149; 546/153; 356/164; 546/165; 546/192; 546/141
[58] Field of Search ...................... 260/293.65, 293.72; 544/105, 178, 173; 546/141, 149, 153, 165, 164, 192; 424/248, 267, 258

[56] References Cited

U.S. PATENT DOCUMENTS

| 2,647,122 | 7/1953 | Archer et al. | 260/293.65 |
| 2,662,886 | 12/1953 | Ruddy et al. | 260/293.72 |

FOREIGN PATENT DOCUMENTS

| 1164152 | 9/1964 | Fed. Rep. of Germany | 544/178 |
| 1173722 | 1/1965 | Fed. Rep. of Germany | 544/178 |
| 1198125 | 8/1965 | Fed. Rep. of Germany | 544/178 |

OTHER PUBLICATIONS

Cannata et al. "Tetrahedron" vol. 27 pp. 5247–5245 (1971).

Primary Examiner—Henry R. Jiles
Assistant Examiner—Robert T. Bond

Attorney, Agent, or Firm—Jon S. Saxe; George M. Gould; Peter R. Shearer

[57] ABSTRACT

Heterocyclic compounds characterized by the formula

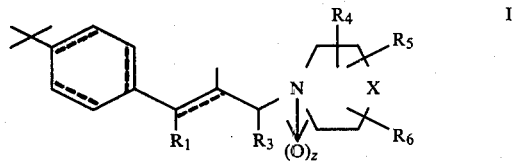

wherein $R_1$, $R_3$, $R_4$, $R_5$, $R_6$, X and z are as hereinafter set forth, prepared, inter alia, by reacting a compound characterized by the formula

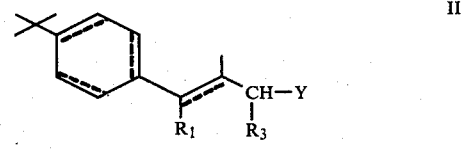

with an amine characterized by the formula

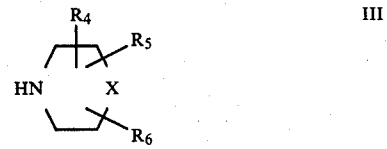

wherein $R_1$, $R_3$, $R_4$, $R_5$, $R_6$, X and Y are as hereinafter set forth, are described. The end products are useful as fungicidal agents.

174 Claims, No Drawings

HETEROCYCLICS USEFUL AS FUNGICIDES AND FUNGICIDAL COMPOSITIONS THEREOF

BRIEF SUMMARY OF THE INVENTION

The invention relates to heterocyclic compounds of the formula

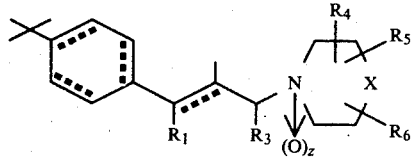

I wherein $R_1$, $R_3$, $R_4$, $R_5$, $R_6$, X and z are as hereinafter described.

In another aspect, the invention relates to fungicidal compositions and methods.

In yet another aspect, the invention relates to compounds useful as intermediates.

DETAILED DESCRIPTION OF THE INVENTION

The present invention comprises heterocyclic compounds of the formula

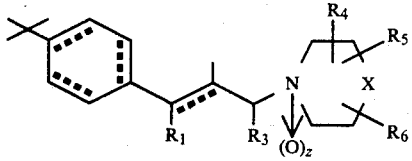

I wherein $R_1$ and $R_3$, individually, are hydrogen or methyl; $R_4$, $R_5$ and $R_6$, individually, are hydrogen or alkyl of 1 to 4 carbon atoms, and two of $R_4$, $R_5$ and $R_6$ can each be bonded to the same carbon or together can form a fused alicyclic or aromatic 6-membered ring; X is methylene or an oxygen atom;
z is zero or 1 and the dotted bonds can be hydrogenated, and acid addition salts of those compounds of formula I which are basic.

As used herein, the term "alkyl" denotes a straight-chain or branched-chain hydrocarbon group containing from 1 to 4 carbon atoms, such as, methyl, ethyl, propyl or isopropyl.

Exemplary of the salts of compounds of formula I which are basic are salts with physiologically acceptable acids. These include, in particular, salts formed with hydrohalic acids, for example, hydrochloric acid and hydrobromic acid, phosphoric acid, nitric acid, monofunctional and bifunctional carboxylic acids and hyroxycarboxylic acids, for example, acetic acid, maleic acid, succinic acid, fumaric acid, tartaric acid, citric acid, salicylic acid, sorbic acid and lactic acid, and sulfonic acids, for example, 1,5-naphthalene-disulfonic acid. Salts of this type are prepared in a known manner.

The compounds of formula I and acid addition salts of those compounds which are basic can be prepared by
(a) reacting a halide of the formula

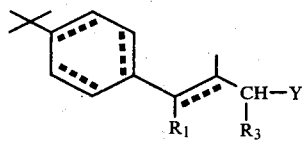

II wherein $R_1$, $R_3$ and the dotted bonds are as previously described, and Y is chlorine, bromine or iodine,
with an amine of the formula

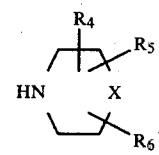

III wherein $R_4$, $R_5$, $R_6$ and X are as previously described, or
(b) catalytically hydrogenating or reducing with formic acid the aliphatic double bond in a compound of the formula

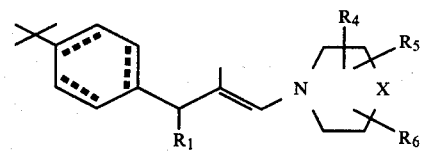

IV wherein $R_1$, $R_4$, $R_5$, $R_6$, X and the dotted bonds are as previously described, or
(c) reacting a compound of the formula

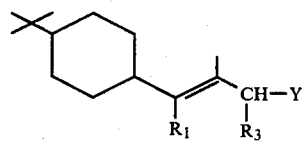

V wherein $R_1$, $R_3$ and Y are as previously described, with an amine of formula III, or
(d) catalytically hydrogenating a compound of the formula

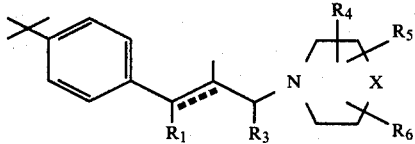

VI wherein $R_1$, $R_3$, $R_4$, $R_5$, $R_6$, X and the dotted bond are as previously described, or
(e) treating a compound of the formula

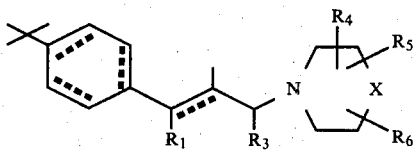

VII wherein $R_1$, $R_3$, $R_4$, $R_5$, $R_6$, X and the dotted bonds are as previously described,
with hydrogen peroxide or a peracid, or
(f) converting a compound of formula I which is basic into a salt with an acid in a known manner.

The Roman numerals mentioned in the following text relate to the structural formulas given earlier and/or to the structural formulas given in the following Formula Schemes and/or to the structural formulas given in the description in connection with the preparation of the starting materials. Some of the formulas given in the text are elaborated in two Formula Schemes A and B. Thus, for example, formula I hereinbefore includes all of the formulas given in Formula Scheme A with the exception of formulas IIa, IIb and IV. In Formula Schemes A and B, the symbols $R_1$, $R_3$, $R_4$, $R_5$, $R_6$, X and Y and the dotted bonds are as previously described. In Formula Scheme B, Et is ethyl and Ac is acetyl.

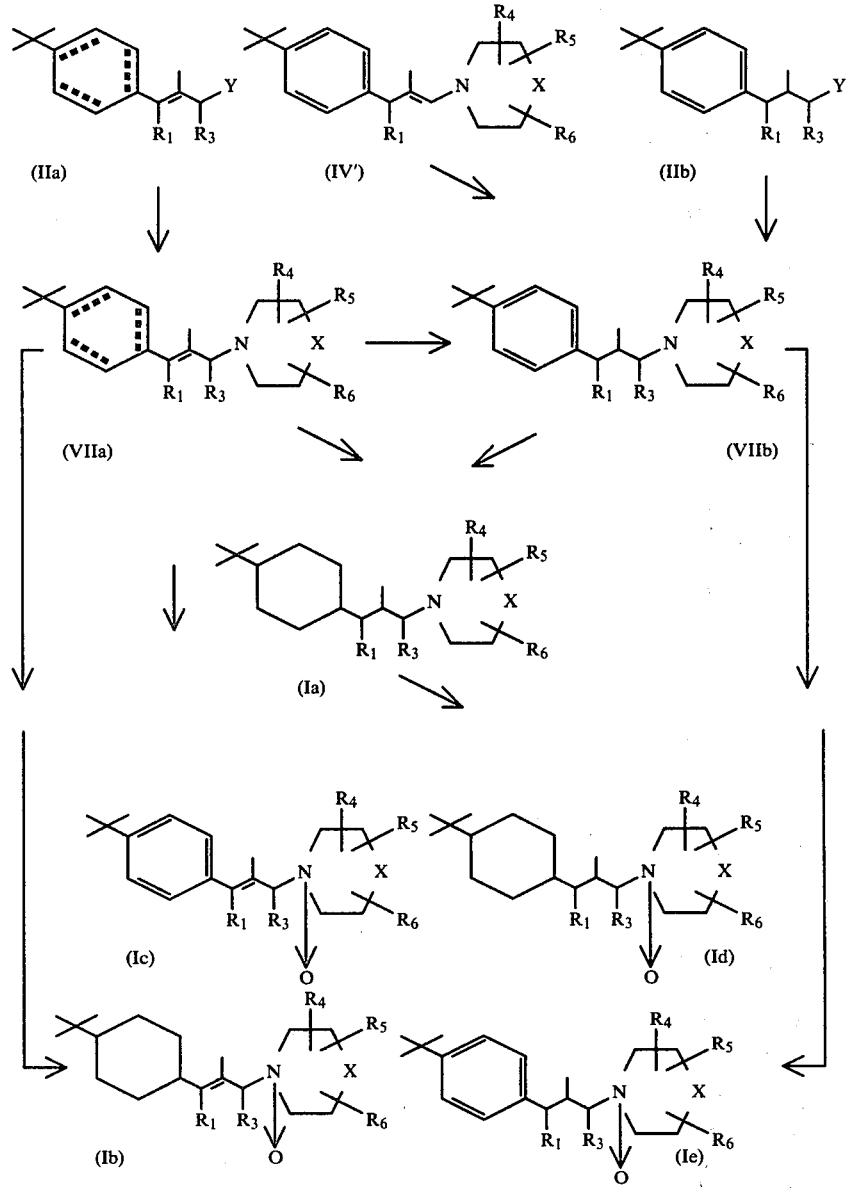

Formula Scheme B

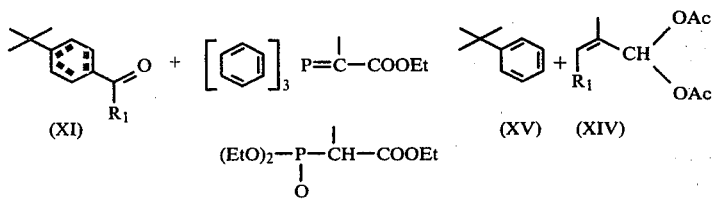

Formula Scheme B

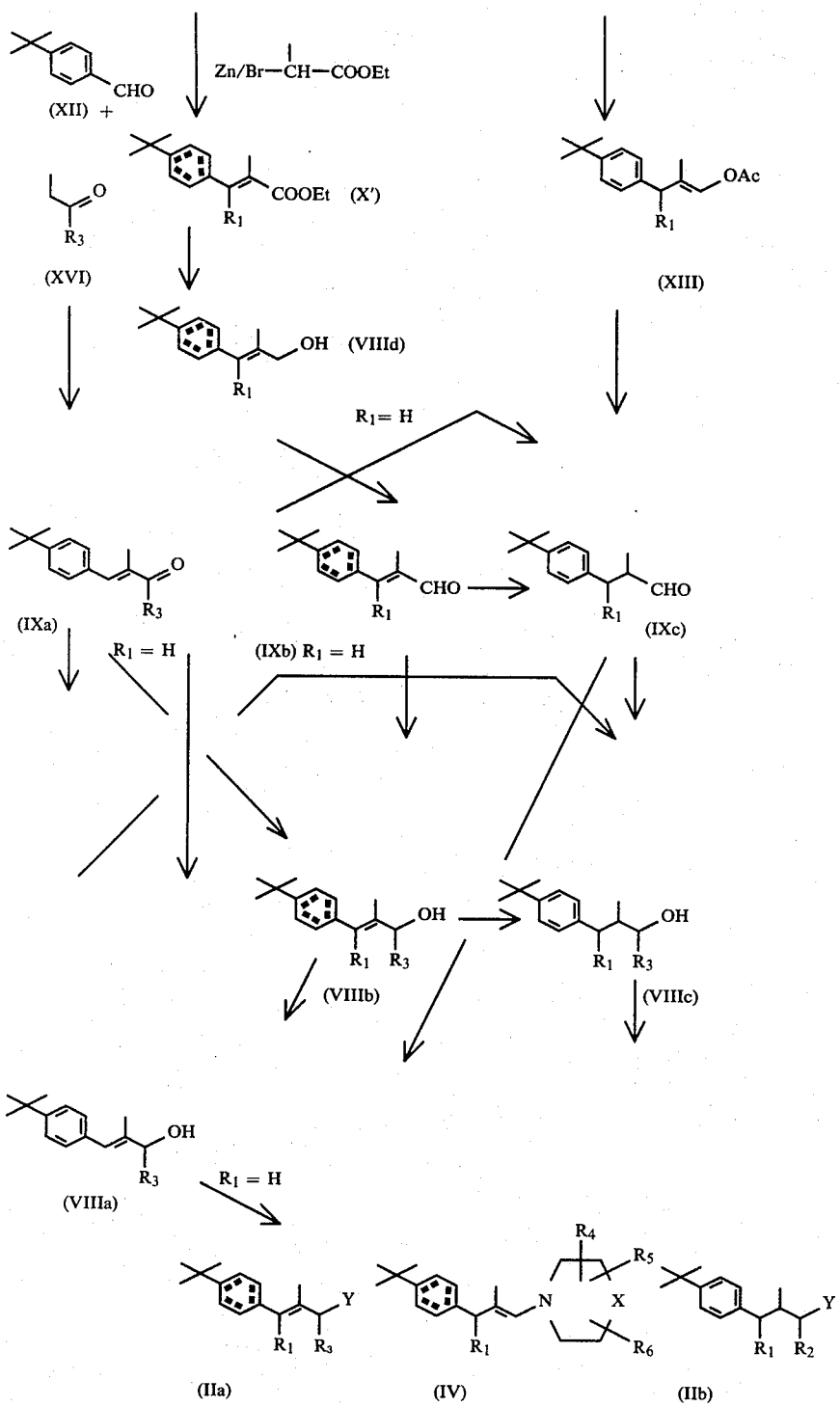

According to process embodiment (a), a halide of formula II is reacted with an amine of formula III in an inert solvent, preferably an ether, such as, diethyl ether, tetrahydrofuran or dioxane, in the presence of a base such as, for example, triethylamine or an excess of the amine of formula III.

When a halide of formula IIa is used as the starting material, diethyl ether is preferably used as the inert solvent. A particularly suitable reaction temperature lies in the range of from about 0° C. to the reflux temperature of the reaction mixture. The reaction is preferably carried out at the boiling point of the reaction mixture.

When a halide of formula IIb is reacted with an amine of formula III, a high boiling alcohol is preferably used as the inert solvent. Ethylene glycol or glycerol is particularly preferred. The reaction is preferably carried out at a temperature in the range of from about 50° C. to about 150° C. In a particularly preferred aspect, the reaction is carried out using ethylene glycol as the inert solvent and at a temperature of 100°-110° C.

According to process embodiment (b), a compound of formula IV is catalytically hydrogenated or is reduced with formic acid. Particularly suitable catalysts are noble metal catalysts, for example, platinum, palladium (optionally precipitated onto charcoal) and Raney nickel. Palladium-on-charcoal is the preferred catalyst. Suitable inert solvents for the catalytic hydrogenation are hydrocarbons, such as, benzene, toluene or xylene, and alcohols, such as, methanol or ethanol. Toluene is the preferred inert solvent. The catalytic hydrogenation is advantageously carried out at a temperature in the range of from about 0° C. to about 50° C., preferably at room temperature. The reduction of a compound of formula IV with formic acid is preferably carried out in the absence of a solvent. Formic acid is added dropwise to a compound of formula IV at a temperature in the range of from 0° C. to 100° C., preferably at 50°-70° C., if necessary with cooling.

According to process embodiment (c), a compound of formula V is reacted with an amine of formula III under the conditions described earlier in connection with process embodiment (a).

According to process embodiment (d), a compound of formula VI is catalytically hydrogenated. Platinum or palladium is preferably used as the catalyst, and water or alcohol is used as the solvent. In order to avoid a possible hydrogenolysis, at least one equivalent of acid, preferably hydrochloric acid, is added to the catalytic hydrogenation mixture. When a perhydrogenation is desired, the catalytic hydrogenation is carried out using platinum in glacial acetic acid with the addition of perchloric acid. The aromatic ring is completely hydrogenated under these conditions.

According to process embodiment (e), a compound of formula VII is treated with hydrogen peroxide or a peracid. When a compound of formula Ia, VIIa or VIIb, see Formula Scheme A, is used as the starting material, the treatment is carried out with hydrogen peroxide. In this case, an alcohol, such as, methanol, ethanol or isopropanol, is used as the solvent, with isopropanol being preferred. The treatment with hydrogen peroxide is preferably carried out at a temperature in the range of from about 0° C. to about 50° C., especially at 40° C. When a compound of formula Ia or VIIb is used as the starting material, the treatment is preferably carried out with a peracid, for example, peracetic acid, perbenzoic acid, m-chloroperbenzoic acid, peradipic acid, or the like, or with hydrogen peroxide in a corresponding acid or acid anhydride. A halogenated hydrocarbon, such as, methylene chloride, chloroform or ethylene chloride, is preferably used as the solvent when a peracid is used. Suitable treatment temperatures are the same as those mentioned earlier in connection with the treatment with hydrogen peroxide.

Preferred compounds of formula I are:
1-[3-p-Tert.butyl-phenyl)-2-methyl-propyl]-piperidine,
1-[3-(4-tert.butyl-cyclohexyl)-2-methyl-propyl]-piperidine,
1-[3-(p-tert.butyl-phenyl)-2-methyl-propyl)-3-methyl-piperidine,
1-[3-(4-tert.butyl-cyclohexyl)-2-methyl-propyl]-3-methyl-piperidine,
4-[3-(p-tert.butyl-phenyl)-2-methyl-propyl]-2,6-dimethyl-morpholine,
1-[3-(p-tert.butyl-phenyl)-2-methyl-propyl]-3-ethyl-piperidine,
1-[3-(4-tert.butyl-cyclohexyl)-2-methyl-propyl]-3-ethyl-piperidine,
1-[3-(p-tert.butyl-phenyl)-2-methyl-propyl]-3,4-dimethyl-piperidine,
1-[3-(p-tert.butyl-phenyl)-2-methyl-propyl]-3,5-dimethyl-piperidine,
1-[3-(4-tert.butyl-cyclohexyl)-2-methyl-propyl]-3,5-dimethyl-piperidine,
1-[3-(p-tert.butyl-phenyl)-2,3-dimethyl-2-propenyl]-piperidine,
1-[3-(p-tert.butyl-phenyl)-2,3-dimethyl-propyl]-piperidine,
1-[3-(4-tert.butyl-cyclohexyl)-2-methyl-2-propenyl]-3-methyl-piperidine,
2-[3-(p-tert.butyl-phenyl)-2-methyl-propyl]-decahydroisoquinoline and
1-[3-(p-tert.butyl-phenyl)-2-methyl-propyl]-decahydroquinoline.

Some of the starting materials of formulas II, IV, V, VI and VII are novel.

The compounds of formulas VI and VII are prepared by alkylating an amine of formula III with a halide of formula II or V. The alkylation is carried out in the same manner as described earlier in connection with process embodiment (a).

The halides can be prepared in a known manner from a corresponding alcohol of the formula

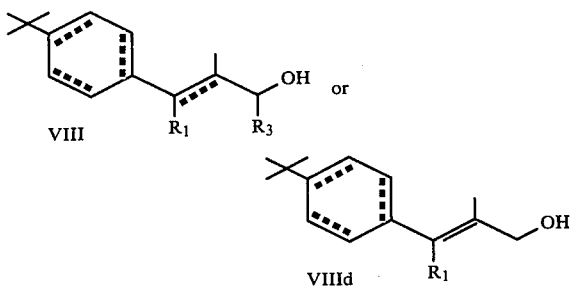

wherein $R_1$ and $R_3$ and the dotted bonds are as previously described,
by treatment with a phosphorus halide, for example, phosphorus tribromide, phosphorus trichloride, phosphorus pentabromide or phosphorus pentachloride, with or without the addition of a tertiary base.

An alcohol of formula VIII or VIIId is obtained in a known manner from a compound of the formula

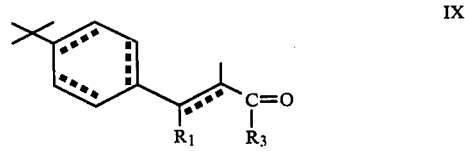

or

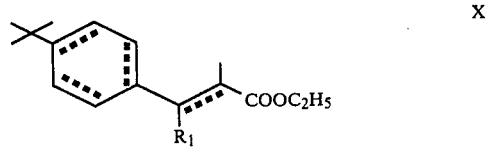

wherein $R_1$, $R_3$ and the dotted bonds are as previously described, by reduction with a suitable complex hydride. Suitable complex hydrides for the reduction of a compound of formula IX are, for example, borohydrides, such as, sodium borohydride or alanates, such as, lithium aluminum hydride. Lithium aluminum hydride is suitable for the reduction of a compound of formula X.

The compounds of formulas IX and X are obtained from an aldehyde or ketone of the formula

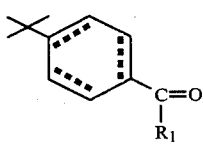

XI wherein $R_1$ and the dotted bonds are as previously described, by means of a Wittig reaction, Horner reaction or Reformatzky reaction, see Formula Scheme B.

Synthesis (1974), page 122 et seq. is referred to as an example of the Wittig reaction and the Horner reaction. The relevant secondary literature is also cited in this literature reference. Examples of the Reformatzky reaction are described in Bull. Soc. Chim. France (1961), page 2145 et seq. A detailed bibliography for the Reformatzky reaction is also given in the latter literature reference.

In order to prepare a compound of formula IXa, wherein $R_3$ is methyl or $R_3$ is hydrogen, the aldehyde of formula XII is reacted with a ketone or aldehyde of formula XVI under the conditions of a Claisen-Schmidt condensation in a known manner. The relevant literature is given in "Namenreaktionen der organischen Chemie", Dr. Alfred Hüthig Verlag GmbH, Heidelberg 1961, page 94.

A compound of formula IXc is prepared from a compound of formula XIII by saponification in a known manner. The saponification is carried out, for example, as described in Bull. Soc. Chim. France (1961), page 1194 et seq. A compound of formula XIII is prepared from the compound of formula XV and a compound of formula XIV by a Friedel-Crafts reaction, also in a known manner. The Friedel-Crafts reaction can be carried out, for example, in an analogous manner to the examples which are given in the aforementioned literature reference.

A compound of formula VIIId is oxidized to a compound of formula IXb in a known manner. For example, the methods described in J. Org. Chem. 39, 3304 (1974) can be used.

A compound of formula IXb or IXc can be converted into a compound of formula VIIIb or VIIIc in a known manner by means of a Grignard reaction. When $R_3$ in a compound of formula IXa is hydrogen, a compound of formula VIIIb, in which $R_3$ is other than hydrogen is also obtained by means of a Grignard reaction. With respect to the Grignard reaction, the monograph "Grignard Reactions of Nonmetallic Substrates", Verlag Prentice-Hall Inc., New York 1954 is referred to.

A compound of formula IXa, IXb, VIIIa or VIIIb is converted into a compound of formula IXc or VIIIc in a known manner by dissolution in an alcohol, preferably methanol or ethanol, optionally with the addition of water and water-soluble inorganic bases, for example, sodium carbonate, potassium carbonate or calcium hydroxide, and hydrogenation at room temperature in the presence of palladium/charcoal.

A compound of formula IV, see Formula Scheme B, is prepared from an aldehyde of formula IXc by reaction with an amine of formula III. For this purpose, an excess of the amine of formula III is added to the aldehyde and the mixture is heated under reflux in benzene or toluene. The water which forms is distilled azeotropically, see "Advances in Organic Chemistry", Vol. 4, pp. 9 et seq., Verlag Interscience Publishers, New York, London, 1963.

Preferred starting materials of formula IXb and IXc hereinbefore are:
p-Tert.butyl-α-methyl-cinnamaldehyde,
p-tert.butyl-α,β-dimethyl-cinnamaldehyde,
3-(p-tert.butyl-phenyl)-2,3-dimethyl-propionaldehyde and
3-(p-tert.butyl-phenyl)-2-methyl-propionaldehyde.

Preferred starting materials of formula IIa hereinbefore are:
3-(p-Tert.butyl-phenyl)-2-methyl-allyl bromide,
3-(p-tert.butyl-phenyl)-1,2-dimethyl-allyl bromide,
3-(p-tert.butyl-phenyl)-2,3-dimethyl-allyl bromide,
3-(p-tert.butyl-phenyl)-1,2,3-trimethyl-allyl bromide,
3-(4-tert.butyl-cyclohexyl)-2-methyl-allyl bromide,
3-(4-tert.butyl-cyclohexyl)-1,2-dimethyl-allyl bromide,
3-(4-tert.butyl-cyclohexyl)-2,3-dimethyl-allyl bromide and
3-(4-tert.butyl-cyclohexyl)-1,2,3-trimethyl-allyl bromide.

Preferred starting materials of formula IIb hereinbefore are:
3-(p-Tert.butyl-phenyl)-2-methyl-propyl bromide,
3-(p-tert.butyl-phenyl)-1,2-dimethyl-propyl bromide,
3-(p-tert.butyl-phenyl)-2,3-dimethyl-propyl bromide,
3-(p-tert.butyl-phenyl)-1,2,3-trimethyl-propyl bromide,
3-(4-tert.butyl-cyclohexyl)-2-methyl-propyl bromide,
3-(4-tert.butyl-cyclohexyl)-1,2-dimethyl-propyl bromide,
3-(4-tert.butyl-cyclohexyl)-2,3-dimethyl-propyl bromide and
3-(4-tert.butyl-cyclohexyl)-1,2,3-trimethyl-propyl bromide.

Preferred starting materials of formula IV hereinbefore are:
1-[3-(p-Tert.butyl-phenyl)-2-methyl-1-propenyl]-piperidine,
1-[3-(p-tert.butyl-phenyl)-2-methyl-1-propenyl]-3-methyl-piperidine,
4-[3-(p-tert.butyl-phenyl)-2-methyl-1-propenyl]-2,6-dimethyl-morpholine,
1-[3-(p-tert.butyl-phenyl)-2-methyl-1-propenyl]-3,4-dimethyl-piperidine,
1-[3-(p-tert.butyl-phenyl)-2-methyl-1-propenyl]-3-ethyl-piperidine,
1-[3-(p-tert.butyl-phenyl)-2-methyl-1-propenyl]-3,5-dimethyl-piperidine,
1-[3-(p-tert.butyl-phenyl)-2-methyl-1-propenyl]-decahydroquinoline and
2-[3-(p-tert.butyl-phenyl)-2-methyl-1-propenyl]-decahydroisoquinoline.

It is not necessary to isolate the compounds of formula IV. They can be converted directly into compounds of formula VIIb, without working up, either by adding formic acid or by hydrogenation.

The compounds of formula I possess fungicidal activity and can accordingly be used for combatting fungi in agriculture and in horticulture. The compounds are particularly suitable for combatting powdery mildew fungi, for example, *Erysiphe graminis* (powdery mildew of cereals), *Erysiphe cichoracearum* (powdery mildew of cucumbers), *Podosphaera leucotricha* (powdery mildew of apples), *Sphaerotheca pannosa* (powdery mildew of roses) and *Oidium tuckeri* (powdery mildew of vines), rust diseases such as those of the genera Puccinia, Uromyces and Hemileia, especially *Puccinia graminis* (stem rust of cereals), *Puccinia coronata* (crown rust of oats), *Puccinia sorghi* (corn rust), *Puccinia striiformis* (stripe rust of wheat), *Puccinia recondita* (leaf rust of cereals), *Uromyces fabae* and *appendiculatus* (bean rusts), as well as *Hemileia vastatrix* (coffee rust) and *Phragmidium mucronatum* (leaf rust of roses).

Furthermore, the compounds of formula I are also active against the following phytopathogenic fungi:

*Ustilago avenae* (loose smut of oats), *Venturia inaequalis* (apple scab), *Cercospora arachidicola* (peanut early leaf spot), *Ophiobolus graminis* (cereal take-all), *Septoria nodorum* (cereal leaf spot) or *Marssonina rosae* (rose blackspot). The compounds of formula I possess pronounced subsidiary activity against various species of the following genera: Rhizoctonia, Tilletia and Helminthosporium, and also, in part, against Peronospora, Coniophora, Lenzites, Corticium, Thielaviopsis and Fusarium.

Furthermore, compounds of formula I are also active against phythopathogenic bacteria such as, for example, *Xanthomonas vesicatoria*, *Xanthomonas oryzae* and other Xanthomonades as well as against various species of Erwinia such as *Erwinia tracheiphila*.

The compounds of formula I are also active as insecticides and acaricides, and, to some extent, insect growth-regulating effects and anti-feedant effects are also found. Thus, for example, 1-[3-(p-tert.butyl-phenyl)-2-methyl-propyl]-3,4-dimethyl-piperidine showed a 100% activity in the larvicide test with *Leptinotarsa decemlineata* at a dosage of $10^{-6}$ g/cm$^2$ and a 50% activity at a dosage of $10^{-7}$ g/cm$^2$.

As will be evident from the following biological tests, the compounds of formula I are active under greenhouse conditions even at a concentration of as little as 5 mg to 500 mg of active ingredient, that is, a compound of formula I, per liter of spray liquor. In the open, concentrations of 100 g. to 2,500 g. of active ingredient per hectare and per treatment are advantageously used. For example, in order to combat powdery mildew of cereals successfully, it is advantageous to use a concentration in the range of from about 200 g. to about 1,000 g., preferably 200 g. to 600 g., of active ingredient per hectare and per application. For combatting cereal rust, it is advantageous to use concentrations in the range of from about 500 g. to about 2,500 g., and particularly preferably—in the case of the most active members—in the range of from about 500 g. to about 2,000 g., of active ingredient per hectare and per application.

Also, the compounds of formula I display a high systemic activity. Untreated parts of the plants can also be protected as a result of secondary distribution of the active ingredient (gas phase action).

For practical purposes, the compounds of formula I can be said to be substantially non-toxic to vertebrates. The toxicity of the compounds of formula I is on average above 1,000 mg per kg of body weight in the acute toxicity test on mice. Individual members show LD$_{50}$ values, determined on mice, of between 400 and 1,000 mg per kg of body weight, while other members show LD$_{50}$ values which are between 1,000 and 10,000 mg kg of body weight in the acute toxicity test on mice.

The biological tests described hereinafter illustrate the activity of the compounds of formula I, the results are summarized in the Tables which follow.

(a) *Erysiphe graminis*

30–40 barley seedlings of the HERTA variety (distributed on 2 pots of 7 cm diameter), the seedlings being in each case in the one-leaf stage, were thoroughly sprayed from all sides with an aqueous dispersion of the test substance (processed in the usual manner as a sprayable powder) and were then grown in a greenhouse at 22°–26° C. and 80% relative atmospheric humidity with a light period of 16 hours. The infection was effected 2 days after the treatment by dusting the test plants with conidia of *Erysiphe graminis*. 7 days after the infection, the leaf surface infected by *Erysiphe graminis* was determined in % relative to the leaf surface of the infected untreated control. The results are summarised in Table I hereinafter.

(b) *Puccinia coronata*

30–40 oat seedlings of the FLAEMINGSKRONE variety (distributed on 2 pots of 7 cm diameter), each seedling being in the one-leaf stage, were thoroughly sprayed from all sides with an aqueous dispersion of the test substance (processed in the usual manner as a sprayable powder) and were then grown in a climatically controlled chamber at 17° C. and 70–80% relative atmospheric humidity with a light period of 16 hours. After 2 days, the test plants were infected by spraying with uredospores (300,000 spores/ml) of *Puccinia coronata* suspended in distilled water. The plants were then incubated in the dark for 24 hours at 20° C. and an atmospheric humidity above 90%, and were subsequently moved into a greenhouse at a temperature of 22°–26° C. and a relative atmospheric humidity of 70% with a light period of 18 hours. On the 9th day after infection, the leaf surface infected by *Puccinia coronata* was determined in % relative to the infected untreated control. The results are summarised in Table I hereinafter.

(c) *Venturia inaequalis*

3 small apple plants (distributed in 3 pots of 5 cm diameter) raised from seeds of the GOLDEN DELICIOUS variety, the plants being in the 4- to 5-leaf stage, were thoroughly sprayed on all sides with an aqueous dispersion of the test substance (processed in the usual manner as a sprayable powder). The treated plants were then grown for 2 days at 17° C. and 70–80% relative atmospheric humidity with a light period of 14 hours. Thereafter, the plants were infected by spraying with a suspension of conidia of *Venturia inaequalis* in distilled water (200,000 conidia/ml). After the infection, the plants were incubated in the dark for 48 hours at 16°–18° C. and a relative atmospheric humidity of above 90%, and were then moved to a shaded greenhouse at a temperature of 22°–26° C. and a relative atmospheric humidity of above 80%. On the 13th day after the infection, the leaf surface infected by *Venturia inaequalis* was determined relative to that of the infected untreated control. The results are summarised in Table II hereinafter.

TABLE I

| Test substance | Concentration (in mg/l of spray liquor) | Activity (in %) Erysiphe graminis | Activity (in %) Puccinia coronata |
|---|---|---|---|
| 1-[3-p-Tert.butyl-phenyl)-2-methyl-propyl]-piperidine | 500 | 100 | 100 |
| | 160 | 100 | 93 |
| | 50 | 100 | 75 |
| | 16 | 90 | 35 |
| | 5 | 60 | 5 |
| 1-[3-(p-Tert.butyl-phenyl)-2-methyl-propyl]-3-methyl-piperidine | 500 | 100 | 100 |
| | 160 | 100 | 100 |
| | 50 | 95 | 80 |
| | 16 | 95 | 25 |
| | 5 | 75 | 0 |
| 4-[3-(p-Tert.butyl-phenyl)-2-methyl-propyl]-2,6-dimethyl-morpholine | 500 | 100 | 100 |
| | 160 | 100 | 95 |
| | 50 | 100 | 50 |
| | 16 | 97 | 7 |
| | 5 | 40 | 0 |
| 1-[3-(p-Tert.butyl-phenyl)-2-methyl-propyl]-piperidine 1-oxide | 500 | 100 | 100 |
| | 160 | 100 | 45 |
| | 50 | 98 | 20 |
| | 16 | 98 | 0 |
| | 5 | 95 | 0 |
| 1-[3-(4-Tert.butyl-cyclohexyl)-2-methyl-propyl]-piperidine | 500 | 100 | 100 |
| | 160 | 100 | 100 |
| | 50 | 100 | 80 |
| | 16 | 85 | 20 |
| | 5 | 0 | 0 |
| 1-[3-(4-Tert.butyl-cyclohexyl)-2-methyl-propyl]-3-methyl-piperidine | 500 | 100 | 100 |
| | 160 | 100 | 100 |
| | 50 | 100 | 100 |
| | 16 | 40 | 70 |
| | 5 | 0 | 15 |
| 1-[3-(p-Tert.butyl-phenyl)-2-methyl-propyl]-3,4-dimethyl-piperidine | 500 | 100 | 100 |
| | 160 | 100 | 100 |
| | 50 | 98 | 95 |
| | 16 | 93 | 30 |
| | 5 | 55 | 0 |
| 1-[3-(p-Tert.butyl-phenyl)-2-methyl-propyl]-3-ethyl-piperidine | 500 | 100 | 100 |
| | 160 | 95 | 100 |
| | 50 | 90 | 98 |
| | 16 | 80 | 45 |
| | 5 | 75 | 0 |
| 1-[3-(p-Tert.butyl-phenyl)-2-methyl-propyl]-2-ethyl-piperidine | 500 | 100 | 100 |
| | 160 | 100 | 45 |
| | 50 | 93 | 10 |
| | 16 | 85 | 0 |
| | 5 | 65 | 0 |
| 1-[3-(p-Tert.butyl-phenyl)-2-methyl-propyl]-3,3-dimethyl-piperidine | 500 | 100 | 98 |
| | 160 | 100 | 20 |
| | 50 | 95 | 0 |
| | 16 | 75 | 0 |
| | 5 | 60 | 0 |
| 1-[3-(p-Tert.butyl-phenyl)-1,2-dimethyl-propyl]-piperidine | 500 | 100 | 100 |
| | 160 | 100 | 90 |
| | 50 | 93 | 75 |
| | 16 | 65 | 35 |
| | 5 | 55 | 0 |
| 1-[3-(p-Tert.butyl-phenyl)-2-methyl-propyl]-4-ethyl-piperidine | 500 | 100 | 100 |
| | 160 | 88 | 98 |
| | 50 | 88 | 93 |
| | 16 | 85 | 30 |
| | 5 | 55 | 0 |
| 1-[3-(p-Tert.butyl-phenyl)-2-methyl-propyl]-3,5-dimethyl-piperidine | 500 | 100 | 100 |
| | 160 | 100 | 100 |
| | 50 | 95 | 95 |
| | 16 | 85 | 10 |
| | 5 | 10 | 0 |
| 1-[3-(p-Tert.butyl-phenyl)-2-methyl-propyl]-3-methyl-piperidine 1-oxide | 500 | 100 | 100 |
| | 160 | 100 | 98 |
| | 50 | 100 | 85 |
| | 16 | 98 | 40 |
| | 5 | 93 | 25 |
| 4-[3-(p-Tert.butyl-phenyl)-2-methyl-propyl]-2,6-dimethyl-morpholine 4-oxide | 500 | 100 | 100 |
| | 160 | 100 | 95 |
| | 50 | 100 | 75 |
| | 16 | 98 | 15 |
| | 5 | 85 | 0 |
| 1-[3-(p-Tert.butyl-phenyl)-2-methyl-2-propenyl]-piperidine | 500 | 100 | 100 |
| | 160 | 100 | 85 |
| | 50 | 100 | 35 |
| | 16 | 100 | 15 |
| | 5 | 100 | 0 |
| 1-[3-(4-Tert.butyl-cyclohexyl)-2-methyl-2-propenyl]-piperidine | 500 | 100 | 100 |
| | 160 | 95 | 100 |
| | 50 | 93 | 95 |
| | 16 | 75 | 75 |
| | 5 | 10 | 30 |
| 1-[3-(4-Tert.butyl-cyclohexyl)-2-methyl-2-propenyl]-3-methyl-piperidine | 500 | 100 | 100 |
| | 160 | 100 | 100 |
| | 50 | 97 | 100 |
| | 16 | 93 | 98 |
| | 5 | 45 | 35 |
| 4-[3-(4-Tert.butyl-cyclohexyl)-2-methyl-2-propenyl]-2,6-dimethyl-morpholine | 500 | 100 | 100 |
| | 160 | 90 | 100 |
| | 50 | 75 | 100 |
| | 16 | 60 | 80 |
| | 5 | 40 | 10 |
| 4-[3-(4-Tert.butyl-cyclohexyl)-2-methyl-propyl]-2,6-dimethyl-morpholine | 500 | 100 | 100 |
| | 160 | 100 | 90 |
| | 50 | 90 | 30 |
| | 16 | 75 | 10 |
| | 5 | 70 | 0 |
| 1-[3-(4-Tert.butyl-cyclohexyl)-2-methyl-propyl]-piperidine 1-oxide | 500 | 100 | 98 |
| | 160 | 100 | 90 |
| | 50 | 100 | 80 |
| | 16 | 93 | 40 |
| | 5 | 90 | 10 |
| 1-[3-(4-Tert.butyl-cyclohexyl)-2-methyl-propyl]-3-methyl-piperidine 1-oxide | 500 | 100 | 100 |
| | 160 | 95 | 100 |
| | 50 | 90 | 95 |
| | 16 | 85 | 90 |
| | 5 | 70 | 40 |
| 1-[3-(p-Tert.butyl-phenyl)-2-methyl-2-propenyl]-3,5-dimethyl-piperidine | 500 | 100 | 100 |
| | 160 | 100 | 100 |
| | 50 | 90 | 90 |
| | 16 | 80 | 70 |
| | 5 | 60 | 5 |
| 1-[3-(p-Tert.butyl-phenyl)-2-methyl-2-propenyl]-3-ethyl-piperidine | 500 | 100 | 100 |
| | 160 | 100 | 95 |
| | 50 | 100 | 90 |
| | 16 | 87 | 40 |
| | 5 | 60 | 10 |
| 1-[3-(p-Tert.butyl-phenyl)-2-methyl-propyl]-3,5-dimethyl-piperidine 1-oxide | 500 | 100 | 100 |
| | 160 | 100 | 100 |
| | 50 | 100 | 95 |
| | 16 | 90 | 75 |
| | 6 | 90 | 20 |
| 1-[3-(p-Tert.butyl-phenyl)-2-methyl-2-propenyl]-3,4-dimethyl-piperidine | 500 | 100 | 100 |
| | 160 | 100 | 100 |
| | 50 | 97 | 90 |
| | 16 | 95 | 30 |
| | 5 | 70 | 10 |
| 1-[3-(p-Tert.butyl-phenyl)-2-methyl-2-propenyl]-3-ethyl-4-methyl-piperidine | 500 | 100 | 100 |
| | 160 | 95 | 95 |
| | 50 | 90 | 75 |
| | 16 | 80 | 10 |
| | 5 | 70 | 0 |
| 1-[3-(p-Tert.butyl-phenyl)-2-methyl-propyl]-decahydro-isoquinoline | 500 | 100 | 100 |
| | 160 | 100 | 100 |
| | 50 | 98 | 100 |
| | 16 | 95 | 98 |
| | 5 | 93 | 10 |
| 1-[3-(p-Tert.butyl-phenyl)-2-methyl-propyl]-decahydro-quinoline | 500 | 100 | 100 |
| | 160 | 100 | 100 |
| | 50 | 95 | 100 |
| | 16 | 95 | 80 |
| | 5 | 93 | 10 |
| 1-[3-(p-Tert.butyl-phenyl)-2-methyl-2-propenyl]-3-methyl-piperidine | 500 | 100 | 100 |
| | 160 | 100 | 100 |
| | 50 | 95 | 95 |
| | 16 | 75 | 45 |
| | 5 | 30 | 5 |
| 1-[3-(p-Tert.butyl-phenyl)-2-methyl-propyl]-3-ethyl-piperidine 1-oxide | 500 | 100 | 95 |
| | 160 | 100 | 95 |
| | 50 | 98 | 55 |
| | 16 | 92 | 0 |
| | 5 | 85 | 0 |

TABLE I-continued

| Test substance | Concentration (in mg/l of spray liquor) | Activity (in %) Erysiphe graminis | Activity (in %) Puccinia coronata |
|---|---|---|---|
| 1-[3-(p-Tert.butyl-phenyl)-2,3-dimethyl-2-propenyl]-piperidine | 500 | 100 | 100 |
| | 160 | 100 | 100 |
| | 50 | 100 | 100 |
| | 16 | 93 | 90 |
| | 5 | 90 | 75 |
| 1-[3-(p-Tert.butyl-phenyl))-2-methyl-propyl]-3,4-dimethyl-piperidine 1-oxide | 500 | 100 | 100 |
| | 160 | 100 | 95 |
| | 50 | 98 | 75 |
| | 16 | 85 | 30 |
| | 5 | 85 | 0 |
| 1-[3-(4-Tert.butyl-cyclohexyl)-2-methyl-propyl]-3,4-dimethyl-piperidine | 500 | 100 | 100 |
| | 160 | 95 | 90 |
| | 50 | 90 | 40 |
| | 16 | 85 | 10 |
| | 5 | 60 | 0 |
| 1-[3-(4-Tert.butyl-cyclohexyl)-2-methyl-propyl]-3,5-dimethyl-piperidine | 500 | 100 | 100 |
| | 160 | 98 | 100 |
| | 50 | 90 | 95 |
| | 16 | 75 | 20 |
| | 5 | 50 | 10 |
| 1-[3-(4-Tert.butyl-cyclohexyl)-2-methyl-propyl]-3-ethyl-piperidine | 500 | 100 | 100 |
| | 160 | 100 | 100 |
| | 50 | 100 | 100 |
| | 16 | 95 | 80 |
| | 5 | 90 | 0 |
| 4-[3-(p-Tert.butyl-phenyl)-2,3-dimethyl-2-propenyl]-2,6-dimethyl-morpholine | 500 | 100 | 100 |
| | 160 | 98 | 100 |
| | 50 | 80 | 100 |
| | 16 | 75 | 85 |
| | 5 | 30 | 0 |
| 1-[3-(p-Tert.butyl-phenyl)-1,2,3-trimethyl-2-propenyl]-piperidine | 500 | 100 | 100 |
| | 160 | 98 | 100 |
| | 50 | 85 | 100 |
| | 16 | 65 | 90 |
| | 5 | 50 | 35 |
| 1-[3-(p-Tert.butyl-phenyl)-2,3-dimethyl-propyl]-piperidine | 500 | 100 | 100 |
| | 160 | 100 | 100 |
| | 50 | 95 | 98 |
| | 16 | 85 | 95 |
| | 5 | 65 | 40 |

TABLE II

| Test substance | Concentration (in mg/l of spray liquor) | (Venturia inaequalis) Activity (in %) |
|---|---|---|
| 4-[3-(p-Tert.butyl-phenyl)-2-methyl-propyl]-2,6-dimethyl-morpholine 4-oxide | 500 | 100 |
| | 160 | 100 |
| | 50 | 73 |
| | 16 | 60 |
| | 5 | 0 |
| 4-[3-(p-Tert.butyl-phenyl)-2,3-dimethyl-2-propenyl]-2,6-dimethyl-morpholine | 500 | 100 |
| | 160 | 100 |
| | 50 | 60 |
| | 16 | 40 |
| | 5 | 20 |

The fungicidal agents provided by the present invention can be used according to methods of application which are customary in plant protection. A mixture can be dissolved in suitable solvents, converted into emulsions or dispersions or applied to suitable carriers. In addition to the inert carrier materials, conventional insecticidal, acaricidal, bactericidal and/or other fungicidal compounds can also be added to the mixture so that plant protection agents having a broad spectrum of activity are obtained. For example, the present fungicidal agents can contain O,O-dimethyl-S-(1,2-dicarbethoxyethyl)-dithiophosphate, O,O-diethyl-O-(p-nitrophenyl)-thiophosphate, γ-hexachlorocyclohexane, 2,2-bis-(p-ethylphenyl)-1,1-dichloroethane, p-chlorobenzyl-p-chlorophenyl sulphide, 2,2-bis-(p-chlorophenyl)-1,1,1-trichloroethanol, zinc ethylene-bis-dithiocarbamate, N-trichloromethyl-thiotetrahydrophthalimide, sulphur, or the like.

Various inert pulverulent carrier materials such as, for example, kaolin, bentonite, talc, whiting, magnesium carbonate or kieselguhr can be used to prepare pulverulent fungicidal agents of this invention. The active ingredients are mixed with these carrier materials, for example, by grinding them together, or the inert carrier materials are impregnated with a solution of the active ingredients and the solvent is then removed by evaporation, heating or by filtration under reduced pressure. Such pulverulent fungicidal agents can be applied to the plants to be protected in the form of dusting agents using a customary dusting apparatus. Such pulverulent fungicidal agents can be rendered easily wettable with water by adding wetting agents and/or dispersing agents so that they can be used in the form of sprays or aqueous suspensions.

In order to prepare emulsifiable concentrates, the active ingredients can, for example, be mixed with an emulsifying agent or dissolved in an inert solvent and mixed with an emulsifier. Ready-to-use emulsions are obtained by diluting such concentrates with water.

Because of their fungistatic and fungicidal activity, the compounds of formula I are also suitable for combating infections which are caused by fungi and yeasts; for example, those of the genera Candida, Trichophytes or Histoplasma. They are particularly active against Candida species such as *Candida albicans* and are particularly suitable for the local therapy of superficial infections of the skin and of the mucous membranes, in particular of the genital tract, for example, vaginitis, especially that caused by Candida. The preferred form of administration is local. For such application, the compounds are used in the form of ointments, miniature suppositories, suppositories, ovules or other suitable forms.

The pharmaceutical preparations can be prepared in a known manner by mixing a compound of formula I with customary organic or inorganic inert excipients and/or auxiliaries such as water, gelatin, lactose, starch, magnesium stearate, talc, vegetable oils, polyalkylene glycols, petroleum jelly, preservatives, stabilizers, wetting agents, emulsifiers, salts for modifying the osmotic pressure or buffers.

The dosage administered will depend on individual requirements, but a daily administration of 1–2 tablets containing 100 mg. of active ingredient for a few days is a suitable dosage. The ointments appropriately contain 0.3%–5%, preferably 0.5%–2% and particularly preferably 0.5%–1%, of active ingredient. The experimental reports and the results given in Table III hereinafter also provide appropriate information appertaining to the dosage of the active ingredients.

(a) Test: *Candida albicans* in vitro

Method: A standardised suspension of the yeast form of *Candida albicans* strain H 29 (ca 300 cells/5 ml, fifty times the lowest number of germs necessary for starting the culture) is poured into a Rowley and Huber agar nutrient medium, liquefied and cooled to 50° C., simultaneously with suitable formulation solutions. The formulations are dissolved in water or polyethylene glycol (Carbowax 400). Formulations which are soluble neither in water nor in polyethylene glycol are finely suspended. The final concentrations of the formulations in the nutrient medium are 100, 10 and 1 mcg/ml and the final concentration of polyethylene glycol is 5%. Incubation is carried out at 37° C. for 7 days.

Evaluation: Assessment of the fungal growth with the naked eye.

Results: The minimum formulation concentration, in mcg/ml, which completely prevents growth of the fungus is given (MIC). The results of some examples are summarised in Table III hereinafter.

(b) Test: *Trichophyton mentagrophytes* in vitro

Method: A standardised suspension of the yeast form of conidia (spores) of *Trichophyton mentagrophytes* strain 109 (ca fifty times the lowest number of germs necessary for starting the culture) is poured into Rowley and Huber agar nutrient medium, liquefied and cooled to 50° C., simultaneously with suitable formulation solutions. The formulations are dissolved in water or polyethylene glycol (Carbowax 400). Formulations which are soluble neither in water nor in polyethylene glycol are finely suspended. The final concentrations of the formulations in the nutrient medium are 100, 10, 1, 0.1 and 0.01 mcg/ml. The final concentration of polyethylene glycol is 5%. Incubation is carried out at 37° C. for 7 days.

Evaluation: Assessment of the fungal growth with the naked eye.

Results: The minimum formulation concentration, in mcg/ml, which completely prevents growth of the fungus is given (MIC). The results of some tests are summarised in Table III hereinafter.

(c) Test: *Histoplasma capsulatum* in vitro

Method: A standardised suspension of the yeast form of *Histoplasma capsulatum* strain Hist 2 (ca fifty times the lowest number of germs necessary for starting the culture) is poured into Rowley and Huber agar nutrient medium, liquefied and cooled to 50° C., simultaneously with suitable formulation solutions. The formulations are dissolved in water or polyethylene glycol (Carbowax 400). Formulations which are soluble neither in water nor in polyethylene glycol are finely suspended. The final concentration of the formulations in the nutrient medium is 100, 10, 1, 0.1 and 0.01 mcg/ml. The final concentration of polyethylene glycol is 5%. Incubation is carried out at 28° C. for 12 days.

Evaluation: Assessment of the fungal growth with the naked eye.

Results: The minimum formulation concentration, in mcg/ml, which completely prevents growth of the fungus is given (MIC). The results of some examples are summarised in Table III hereinafter.

TABLE III

| | MIC (μg/ml) | | |
|---|---|---|---|
| Test substance | *Candida albicans* | *Trichophyton mentagr.* | *Histoplasma capsulatum* |
| 1-[3-(4-Tert.butyl-cyclohexyl)-2-methyl-propyl]-piperidine | 10 | 0.1 | 0.01 |
| 1-[3-(p-Tert.butyl-phenyl)-2-methyl-propyl]-3-methyl-piperidine | 10 | 1 | 0.1 |
| 1-[3-(4-Tert.butyl-cyclohexyl)-2-methyl-propyl]-3-methyl-piperidine | 10 | | 1 |
| 1-[3-(p-Tert.butyl-phenyl)-2-methyl-propyl]-3,4-dimethyl-piperidine | 10 | 0.1 | 0.01 |
| 4-[3-(p-Tert.butyl-phenyl)-2-methyl-propyl]-2,6-dimethyl-morpholine | 10 | 1 | 0.1 |
| 1-[3-(p-Tert.butyl-phenyl)-2-methyl-propyl]-3-ethyl-4-methyl-piperidine | 10 | | 1 |
| 1-[3-(4-Tert.butyl-cyclohexyl)-2-methyl-propyl]-3-ethyl-4-methyl-piperidine | 10 | 0.01 | 0.01 |
| 1-[3-(4-Tert.butyl-cyclohexyl)-2-methyl-propyl]-3,5-dimethyl-piperidine | 1 | 0.01 | 0.01 |
| 1-[3-(4-Tert.butyl-cyclohexyl)-2-methyl-propyl]-3-ethyl-piperidine | 1 | 0.01 | 0.01 |
| 1-[3-(p-Tert.butyl-phenyl)-2-methyl-propyl]-3-ethyl-piperidine | 1 | 0.01 | 0.01 |
| 1-[3-(p-Tert.butyl-phenyl)-2-methyl-propyl]-3,5-dimethyl-piperidine | 1 | 0.01 | 0.01 |
| 4-[3-(4-Tert.butyl-cyclohexyl)-2-methyl-2-propenyl]-2,6-dimethyl-morpholine | 10 | 100 | 1 |
| 1-[3-(p-Tert.butyl-phenyl)-2-methyl-2-propenyl]-3,5-dimethyl-piperidine | 10 | 1 | 0.01 |
| 1-[3-(p-Tert.butyl-phenyl)-2-methyl-propyl]-3,5-dimethyl-piperidine 1-oxide | 10 | 0.1 | 1 |

MIC = minimum inhibitory concentration.
The values given are in most cases maximum values, i.e. the minimum inhibitory concentration can be lower.
The compounds of formula I also show the antimycotic activity described earlier in "in vivo" experiments.

The following Examples illustrate the present invention:

I. Preparation of the sprayable powders used in the biological experiments and of other formulations:

1. Sprayable powder appropriate for all compounds of formula I

EXAMPLE 1

| | w/w %* |
|---|---|
| Active Ingredient | 25.0 |
| Finely divided hydrated silicic acid | 25.0 |
| Methylhydroxyethylcellulose | 1.0 |
| Sodium oleate | 2.0 |
| Nonylphenol-ethylene oxide adduct | 3.0 |
| Sodium salt of dinaphthylmethane-disulfonic acid | 10.0 |
| Kaolin B 24 | 34.0 |
| | 100.0 |

*Weight percent

The solid active ingredients are mixed with the hydrated silicic acid or liquid active ingredients are taken up on the hydrated silicic acid. The customary additives are added and the mixture is homogeneously mixed in a suitable apparatus. The resulting powder is now finely milled in a suitable grinding apparatus, for example, a pinned disc mill, hammer mill, ball mill, air-jet mill, or the like, and thereafter again mixed.

2. Seed disinfectant appropriate for all compounds of formula I

EXAMPLE 2

|  | % w/w |
| --- | --- |
| Active ingredient | 20.0 |
| Calcium silicate | 20.0 |
| Red iron oxide pigment | 8.0 |
| Roter xanthene colourant (Colour Index: Solvent Red 49) | 0.5 |
| Starch hydrolysate-powder (dextrin) | 2.0 |
| Sulphite pulp spent liquor-powder | 3.2 |
| Sodium butylnaphthylsulphonate | 2.0 |
| Kaolin b 24 | 44.3 |
|  | 100.0 |

The solid active ingredient is mixed with calcium silicate or liquid active ingredient is taken up on calcium silicate. The customary additives are added and the mixture is mixed and milled (see Example 1). The resulting red powder can be used tel quel as a dry disinfectant for seeds or can be diluted with water to form a liquid disinfectant for seeds.

3. Emulsifiable concentrate appropriate for oily compounds of formula I

EXAMPLE 3

|  | g/l |
| --- | --- |
| Active ingredient [for example, 1-[3-(p-tert.-butyl-phenyl)-2-methyl-propyl]-piperidine] | 500 |
| Castor oil-ethyleneoxide-adduct | 100 |
| Calcium salt of dodecylbenzenesulfonic acid | 50 |
| Aromatic solvent (mixture of $C_{10}$-alkylbenzenes) | ad 1000 ml. |

The active substance is dissolved in a portion of the aromatic solvent, the customary additives are added and dissolved, and the mixture is made up to volume with the remainder of the solvent. The resulting product is added to water in order to prepare a ready-for-use spray liquor, whereby there is obtained an emulsion (oil/water) which is stable for hours.

4. Water-soluble concentrate appropriate for water-soluble compounds of formula I

EXAMPLE 4

|  | g/l |
| --- | --- |
| Active ingredient [for example, 1-[3-(p-tert.-butyl-phenyl)-2-methyl-propyl]-piperidine 1-oxide] | 250 |
| Isopropanol | 300 |
| Water, deionized | ad 1000 ml. |

The active ingredient is dissolved in isopropanol and made up to volume with water. The concentrate, which is stable to temperatures as low as $-5°$ C., can be appropriately diluted with water in order to prepare a ready-for-use spray liquor, whereby there is obtained a solution in the form of a molecular dispersion.

EXAMPLE 5

|  | g/l |
| --- | --- |
| Active ingredient [for example, 1-[3-(p-tert.-butyl-phenyl)-2-methyl-propyl]-piperidine 1-oxide] | 250 |
| Dispersion of a copolymeric vinyl acetate/ethylene solid body weight about 50% | 50 |
| Water, deionized | ad 1000 ml. |

The active ingredient is dissolved in a portion of the water, the copolymer dispersion is then stirred in and the mixture is made up to volume with the remainder of the water. The resulting homogeneous dispersion can be diluted with the appropriate amount of water to form a ready-for-use spray liquor. The copolymer dispersion confers to the liquor an improved adhesion to the aerial parts of plants.

5. Formulations appropriate for compounds of formula I which contain a protonisable nitrogen atom This type of formulation contains salts and molecular and addition products of the compounds provided by the invention; for example,

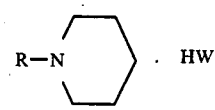

wherein HW is an acid or an acid mixture which preferably has a pK value of less than 5.0.

In this connection, there preferably come into consideration organic acids which form salts which are soluble in water, in mixtures of water and water-soluble solvents and in non-polar solvents.

The salts are preferably prepared in situ during the formulation of the active ingredients by adding a stoichiometric amount of HW in the presence of water and/or organic solvents or solid carrier materials at usual temperatures.

EXAMPLE 6

|  | g/l |
| --- | --- |
| Active ingredient [for example, 4-[3-(p-tert.-butyl-phenyl)-2-methyl-propyl]-2,6-dimethylmorpholine] | 250 |
| Acetic acid (100%) (pK: 4.75) | 35 |
| Lactic acid (90%) (pK: 3.08) | 30 |
| Isopropanol | 300 |
| Water, deionized | ad 1000 ml. |

The active ingredient is dissolved in isopropanol. The lactic acid and the acetic acid are added with stirring, a relatively strong warming-up taking place. The mixture is made up to volume with water. The resulting clear, practically colourless solution (a water-soluble concentrate) can be diluted with water to give a ready-for-use spray liquor.

EXAMPLE 7

|  | g/l |
| --- | --- |
| Active ingredient [for example, 1-[3-(p-tert.-butyl-phenyl)-2-methyl-propyl]-piperidine] | 250 |
| Methanesulfonic acid | 88 |
| Water, deionized | ad 1000 ml. |

The methanesulphonic acid is added dropwise with stirring to a portion of the water, a very strong warming-up taking place. After cooling to room temperature, the mixture is made up to volume with water. The resulting clear, slightly yellowish solution (a water-soluble concentrate) can be diluted with water to give a ready-for-use spray liquor.

EXAMPLE 8

|  | g/l |
|---|---|
| Active ingredient [for example, 1-[3-(p-tert.-butyl-phenyl)-2-methyl-propyl]-piperidine] | 250 |
| Bis-(2-ethylhexyl)-phosphoric acid | 145 |
| Emulsifier | 100(*) |
| Aromatic solvent (mixture of C$_{10}$-alkylbenzenes) | ad 1000 ml. |

(*)Mixture of nonylphenol-ethyleneoxide adducts, dodecylbenzenesulfonic acid calcium salt and solvent.

The active ingredient is dissolved in a portion of the aromatic solvent and then the bis-(2-ethylhexyl)-phosphoric acid is stirred in dropwise, a moderate warming-up taking place. The still warm mixture is treated with the emulsifier, the resulting mixture is cooled to room temperature and made up to volume with the aromatic solvent. In order to prepare a ready-for-use spray liquor, the product obtained (an emulsifiable concentrate) is stirred into water, whereby there is obtained an emulsion (oil/water).

EXAMPLE 9

|  | g/l |
|---|---|
| Active ingredient [for example, 1-[3-(p-tert.-butyl-phenyl)-2-methyl-propyl]-piperidine] | 250 |
| Phosphoric acid monoester and diester of nonyl-phenolpolyglycol ether | 400 |
| Dimethylformamide | 200 |
| 1,1,1-Trichloroethane | ad 1000 ml. |

The active ingredient is dissolved in the dimethylformamide and then the phosphoric acid ester is stirred in dropwise, an appreciable warming-up taking place. After cooling, the mixture is made up to volume with 1,1,1-trichloroethane. In order to prepare a finished spray liquor, the product obtained (an emulsifiable concentrate) is stirred into water, whereby there is obtained an emulsion (oil/water) which is stable for hours.

A typical feature of this formulation is the presence of a tensioactive acid which makes the addition of an emulsifier superfluous.

EXAMPLE 10

|  | w/w % |
|---|---|
| Active ingredient [for example, 1-[3-(p-tert.-butyl-phenyl)-2-methyl-propyl]-piperidine] | 25.0 |
| Sulfamic acid | 9.0 |
| Finely divided hydrated silicic acid | 25.0 |
| Mixture of 85% sodium dioctylsulfosuccinate and 15% sodium benzoate | 1.0 |
| Diammonium hydrogen phosphate | 40.0 |

The active ingredient is mixed with the hydrated silicic acid to give a dry powder. The remaining additives are then admixed and the resulting mixture is finely milled in a suitable grinding apparatus (see Example 1). In order to prepare a finished spray liquor, the product obtained (a water-soluble powder) is diluted with water.

II. PREPARATION OF THE COMPOUNDS OF FORMULA I:

EXAMPLE 11

Preparation of
1-[3-(p-tert.-butyl-phenyl)-2-methyl-propyl]-piperidine 2.9 Kg. of 1-[3-(p-tert.-butyl-phenyl)-2-methyl-1-propenyl]-piperidine are taken up in 1.4 liters of toluene, treated under an atmosphere of nitrogen with 144.8 g. of 5% palladium/carbon and hydrogenated at 35° C. until the hydrogen uptake has been completed. The catalyst is removed by filtration, the toluene is evaporated in vacuo and the residue is distilled. There is obtained pure 1-[3-(p-tert.-butyl-phenyl)-2-methyl-propyl]-piperidine, having a boiling point of 125° C./0.045 Torr.

In an analogous manner,
from 1-[3-(p-tert.butyl-phenyl)-2-methyl-1-propenyl]-3-methyl-piperidine there is obtained 1-[3-(p-tert.butyl-phenyl)-2-methyl-propyl]-3-methyl-piperidine of boiling point 115°-117° C./0.02 Torr,
from 4-[3-(p-tert.butyl-phenyl)-2-methyl-1-propenyl]-morpholine there is obtained 4-[3-(p-tert.butyl-phenyl)-2-methyl-propyl]-morpholine of boiling point 125° C./0.02 Torr, and
from 4-[3-(p-tert.butyl-phenyl)-2-methyl-1-propenyl]-2,6-dimethyl-morpholine there is obtained 4-[3-(p-tert.butyl-phenyl)-2-methyl-propyl]-2,6-dimethyl-morpholine of boiling point 135° C./0.03 Torr.

EXAMPLE 12

Preparation of
1-[3-(p-tert.-butyl-phenyl)-2-methyl-propyl]-3,5-dimethyl-piperidine 67.8 g of 3-(p-tert.butyl-phenyl)-2-methyl-propionaldehyde and 50 g of 3,5-dimethyl-piperidine are heated at reflux in 50 ml of toluene in a water-separator under nitrogen gasification until the water-cleavage has been completed (16 hours). Subsequently, there are added dropwise at room temperature while stirring 16.8 g of formic acid, the temperature rising to 36°-40° C. The mixture is then heated to 80° C. for 1 hour. 165 ml of 2-N hydrochloric acid are added to the cooled solution, the toluene solution is separated, the aqueous-hydrochloric acid solution is made alkaline with 66 ml of 6-N sodium hydroxide and the product is extracted with ether. The combined ether extracts are washed with water, dried over sodium sulphate and evaporated. By distillation there is obtained pure 1-[3-(p-tert.butyl-phenyl)-2-methyl-propyl]-3,5-dimethyl-piperidine of boiling point 113°-114° C./0.09 Torr.

EXAMPLE 13

Preparation of
1-[3-(p-tert.-butyl-phenyl)-2-methyl-propyl]-3-methyl-piperidine 4.45 Kg. of 3-(p-tert.-butyl-phenyl)-2-methyl-propionaldehyde and 2.38 kg. of 3-methyl-piperidine are heated at reflux in 3.42 liters of toluene for 16 hours in a water-separator under nitrogen gasification until the water-cleavage has been completed. 197 G. of 5% palladium/carbon are added at room temperature under nitrogen gasification and the mixture is subsequently hydrogenated until the hydrogen uptake has been completed. The catalyst is then removed by filtration and the toluene evaporated in vacuo. By distillation of the residue, there is obtained pure 1-[3-(p-tert.-butylphenyl)-2-methyl-propyl]-3-methyl-piperidine, having a boiling point of 115°–117° C./0.02 Torr.

In an analogous manner, from 3-(p-tert.butyl-phenyl)-2-methyl-propionaldehyde and 2-methyl-piperidine there is obtained, after hydrogenation, 1-[3-(p-tert.butyl-phenyl)-2-methyl-propyl]-2-methyl-piperidine of boiling point 130°–133° C./0.05 Torr, from 3-(p-tert.butyl-phenyl)-2-methyl-propionaldehyde and 4-methyl-piperidine there is obtained, after hydrogenation, 1-[3-(p-tert.butyl-phenyl)-2-methyl-propyl]-4-methyl-piperidine of boiling point 112°–114° C./0.02 Torr, from 3-(p-tert.butyl-phenyl)-2-methyl-propionaldehyde and 4-ethyl-piperidine there is obtained, after hydrogenation, 1-[3-(p-tert.butyl-phenyl)-2-methyl-propyl]-4-ethyl-piperidine of boiling point 126° C./0.04 Torr, from 3-(p-tert.butyl-phenyl)-2-methyl-propionaldehyde and 2,6-dimethyl-piperidine there is obtained, after hydrogenation, 1-[3-(p-tert.butyl-phenyl)-2-methyl-propyl]-2,6-dimethyl-piperidine of boiling point 126° C./0.005 Torr, from 3-(p-tert.butyl-phenyl)-2-methyl-propionaldehyde and 1,2,3,4-tetrahydroquinoline there is obtained, after hydrogenation, 1-[3-(p-tert.butyl-phenyl)-2-methyl-propyl]-1,2,3,4-tetrahydroquinoline of boiling point 120° C./0.001 Torr, from 3-(p-tert.butyl-phenyl)-2-methyl-propionaldehyde and 1,2,3,4-tetrahydroisoquinoline there is obtained, after hydrogenation, 2-[3-(p-tert.butyl-phenyl)-2-methyl-propyl]-1,2,3,4-tetrahydroisoquinoline of boiling point 168°–172° C./0.03 Torr, from 3-(p-tert.butyl-phenyl)-2-methyl-propionaldehyde and decahydroquinoline there is obtained, after hydrogenation, 1-[3-(p-tert.butyl-phenyl)-2-methyl-propyl]-decahydroquinoline of boiling point 141°–151° C./0.017 Torr, from 3-(p-tert.butyl-phenyl)-2-methyl-propionaldehyde and decahydroisoquinoline there is obtained, after hydrogenation, 2-[3-(p-tert.butyl-phenyl)-2-methyl-propyl]-decahydroisoquinoline of boiling point 140°–148° C./0.017 Torr, from 3-(p-tert.butyl-phenyl)-2-methyl-propionaldehyde and 2-ethyl-piperidine there is obtained, after hydrogenation, 1-[3-(p-tert.butyl-phenyl)-2-methyl-propyl]-2-ethyl-piperidine of boiling point 112°–115° C./0.039 Torr, from 3-(p-tert.butyl-phenyl)-2-methyl-propionaldehyde and 3-ethyl-piperidine there is obtained, after hydrogenation, 1-[3-(p-tert.butyl-phenyl)-2-methyl-propyl]-3-ethyl-piperidine of boiling point 113°–115° C./0.035 Torr, from 3-(p-tert.butyl-phenyl)-2-methyl-propionaldehyde and 2,4-dimethyl-piperidine there is obtained, after hydrogenation, 1-[3-(p-tert.butyl-phenyl)-2-methyl-propyl]-2,4-dimethyl-piperidine of boiling point 110° C./0.039 Torr, from 3-(p-tert.butyl-phenyl)-2-methyl-propionaldehyde and 2,5-dimethyl-piperidine there is obtained, after hydrogenation, 1-[3-(p-tert.butyl-phenyl)-2-methyl-propyl]-2,5-dimethyl-piperidine of boiling point 112° C./0.042 Torr, from 3-(p-tert.butyl-phenyl)-2-methyl-propionaldehyde and 5-ethyl-2-methyl-piperidine there is obtained, after hydrogenation, 1-[3-(p-tert.butyl-phenyl)-2-methyl-propyl]-5-ethyl-2-methyl-piperidine of boiling point 126°–130° C./0.012 Torr, from 3-(p-tert.butyl-phenyl)-2-methyl-propionaldehyde and 3,5-dimethyl-piperidine there is obtained, after hydrogenation, 1-[3-(p-tert-butyl-phenyl)-2-methyl-propyl]-3,5-dimethyl-piperidine of boilint point 129° C./0.001 Torr, from 3-(p-tert.butyl-phenyl)-2-methyl-propionaldehyde and 3,4-dimethyl-piperidine there is obtained, after hydrogenation, 1-[3-(p-tert.butyl-phenyl)-2-methyl-propyl]-3,4-dimethyl-piperidine of boiling point 116°–121° C./0.032 Torr, from 3-(p-tert.butyl-phenyl)-2-methyl-propionaldehyde and 3-ethyl-4-methyl-piperidine there is obtained, after hydrogenation, 1-[3-(p-tert.butyl-phenyl)-2-methyl-propyl]-3-ethyl-4-methyl-piperidine of boiling point 140°–142° C./0.048 Torr, from 3-(p-tert.butyl-phenyl)-2-methyl-propionaldehyde and 2,4,6-trimethyl-piperidine there is obtained, after hydrogenation, 1-[3-(p-tert.butyl-phenyl)-2-methyl-propyl]-2,4,6-trimethyl-piperidine of boiling point 132° C./0.005 Torr, and from 3-(p-tert.butyl-phenyl)-2-methyl-propionaldehyde and 3,3-dimethyl-piperidine there is obtained, after hydrogenation, 1-[3-(p-tert.butyl-phenyl)-2-methyl-propyl]-3,3-dimethyl-piperidine of boiling point 112° C./0.04 Torr.

EXAMPLE 14

Preparation of 1-[3-(p-tert.-butyl-phenyl)-1,2-dimethyl-propyl]-piperidine 21.2 g of 3-(p-tert.butyl-phenyl)-1,2-dimethyl-propyl bromide, 17 g of piperidine and 7.5 g of ethyleneglycol are heated to 110° C. for 60 hours. After cooling, the mixture is treated with 2-N hydrochloric acid and the neutral constituent is extracted with ether. Subsequently, the hydrochloric acid solution is made alkaline with 5-N sodium hydroxide solution and extracted with ether. The combined ether extracts are washed neutral with water, dried over sodium sulphate and evaporated. By distillation there is obtained pure 1-[3-(p-tert.butyl-phenyl)-1,2-dimethyl-propyl]-piperidine (boiling point 125° C./0.005 Torr) in the form of a colourless oil.

EXAMPLE 15

Preparation of 1-[3-(p-tert.-butyl-phenyl)-2-methyl-2-propenyl]-piperidine 35 g of 3-(p-tert.butyl-phenyl)-2-methyl-allyl bromide in 70 ml of ether are added dropwise to a solution of 24.5 g of piperidine in 100 ml of absolute ether and the mixture is heated at reflux for 16 hours. The piperidine hydrobromide is removed by filtration and rinsed with ether. The ether solution is extracted with 2-N hydrochloric acid and made alkaline with 50% sodium hydroxide. The alkaline-aqueous solution is again extracted with ether, washed with water, dried over sodium sulphate and evaporated. By distillation there is obtained pure 1-[3-(p-tert.butyl-phenyl)-2-methyl-2-propenyl]-piperidine of boiling point 96°–98° C./0.03 Torr.

In an analogous manner, from 3-(p-tert.butyl-phenyl)-2-methyl-allyl bromide and 2,6-dimethyl-morpholine there is obtained 4-[3-(p-tert.butyl-phenyl)-2-methyl-2-propenyl]-2,6-dimethyl-morpholine of boiling point 135° C./0.005 Torr, from 3-(4-tert.butyl-cyclohexyl)-2-methyl-allyl bromide and piperidine there is obtained 1-[3-(4-tert.butyl-cyclohexyl)-2-methyl-2-propenyl]-piperidine of boiling point 100°-103° C./0.04 Torr, from 3-(4-tert.butyl-cyclohexyl)-2-methyl-allyl bromide and 3-methyl-piperidine there is obtained 1-[3-(4-tert.butyl-cyclohexyl)-2-methyl-2-propenyl]-3-methyl-piperidine of boiling point 113°-115° C./0.03 Torr, from 3-(4-tert.butyl-cyclohexyl)-2-methyl-allyl bromide and 2,6-dimethyl-morpholine there is obtained 4-[3-(4-tert.butyl-cyclohexyl)-2-methyl-2-propenyl]-2,6-dimethyl-morpholine of boiling point 131°-134° C./0.04 Torr, from 3-(p-tert.butyl-phenyl)-2,3-dimethyl-allyl bromide and piperidine there is obtained 1-[3-(p-tert.butyl-phenyl)-2,3-dimethyl-2-propenyl]-piperidine of boiling point 119° C./0.006 Torr, from 3-(p-tert.butyl-phenyl)-1,2,3-trimethyl-allyl bromide and piperidine there is obtained 1-[3-(p-tert.butyl-phenyl)-1,2,3-trimethyl-2-propenyl]-piperidine of boiling point 154° C./0.03 Torr, from 3-(p-tert.butyl-phenyl)-2-methyl-allyl bromide and 2-ethyl-piperidine there is obtained 1-[3-(p-tert.butyl-phenyl)-2-methyl-2-propenyl]-2-ethyl-piperidine of boiling point 117°-120° C./0.023 Torr, from 3-(p-tert.butyl-phenyl)-2-methyl-allyl bromide and 3-methyl-piperidine there is obtained 1-[3-(p-tert.butyl-phenyl)-2-methyl-2-propenyl]-3-methyl-piperidine of boiling point 118° C./0.042 Torr, from 3-(p-tert.butyl-phenyl)-2-methyl-allyl bromide and 3-ethyl-piperidine there is obtained 1-[3-(p-tert.butyl-phenyl)-2-methyl-2-propenyl]-3-ethyl-piperidine of boiling point 124° C./0.04 Torr, from 3-(p-tert.butyl-phenyl)-2-methyl-allyl bromide and 2,6-dimethyl-piperidine there is obtained 1-[3-(p-tert.butyl-phenyl)-2-methyl-2-propenyl]-2,6-dimethyl-piperidine of boiling point 122°-126° C./0.031 Torr, from 3-(p-tert.butyl-phenyl)-2-methyl-allyl bromide and 2,4-dimethyl-piperidine there is obtained 1-[3-(p-tert.butyl-phenyl)-2-methyl-2-propenyl]-2,4-dimethyl-piperidine of boiling point 154°-156° C./0.025 Torr, from 3-(p-tert.butyl-phenyl)-2-methyl-allyl bromide and 2,5-dimethyl-piperidine there is obtained 1-[3-(p-tert.butyl-phenyl)-2-methyl-2-propenyl]-2,5-dimethyl-piperidine of boiling point 112° C./0.03 Torr, from 3-(p-tert.butyl-phenyl)-2-methyl-allyl bromide and 5-ethyl-2-methyl-piperidine there is obtained 1-[3-(p-tert.butyl-phenyl)-2-methyl-2-propenyl]-5-ethyl-2-methyl-piperidine of boiling point 120° C./0.05 Torr, from 3-(p-tert.butyl-phenyl)-2-methyl-allyl bromide and 3,5-dimethyl-piperidine there is obtained 1-[3-(p-tert.butyl-phenyl)-2-methyl-2-propenyl]-3,5-dimethyl-piperidine of boiling point 120° C./0.04 Torr, from 3-(p-tert.butyl-phenyl)-2-methyl-allyl bromide and 4-ethyl-piperidine there is obtained 1-[3-(p-tert.butyl-phenyl)-2-methyl-2-propenyl]-4-ethyl-piperidine of boiling point 137° C./0.039 Torr, from 3-(p-tert.butyl-phenyl)-2-methyl-allyl bromide and 3,4-dimethyl-piperidine there is obtained 1-[3-(p-tert.butyl-phenyl)-2-methyl-2-propenyl]-3,4-dimethyl-piperidine of boiling point 118° C./0.03 Torr, from 3-(p-tert.butyl-phenyl)-2-methyl-allyl bromide and 3-ethyl-4-methyl-piperidine there is obtained 1-[3-(p-tert.butyl-phenyl)-2-methyl-2-propenyl]-3-ethyl-4-methyl-piperidine of boiling point 146° C./0.05 Torr, from 3-(p-tert.butyl-phenyl)-2-methyl-allyl bromide and 2,4,6-trimethyl-piperidine there is obtained 1-[3-(p-tert.butyl-phenyl)-2-methyl-2-propenyl]-2,4,6-trimethyl-piperidine of boiling point 109° C./0.03 Torr, from 3-(p-tert.butyl-phenyl)-2,3-dimethyl-allyl bromide and 2,6-dimethyl-morpholine there is obtained 4-[3-(p-tert.butyl-phenyl)-2,3-dimethyl-2-propenyl]-2,6-dimethyl-morpholine of boiling point 143°-146° C./0.03 Torr, from 3-(p-tert.butyl-phenyl)-2-methyl-allyl bromide and 3,3-dimethyl-piperidine there is obtained 1-[3-(p-tert.butyl-phenyl)-2-methyl-2-propenyl]-3,3-dimethyl-piperidine of boiling point 126° C./0.05 Torr, from 3-(p-tert.butyl-phenyl)-1,2-dimethyl-allyl bromide and piperidine there is obtained 1-[3-(p-tert.butyl-phenyl)-1,2-dimethyl-2-propenyl]-piperidine of boiling point 127°-129° C./0.035 Torr, from 3-(p-tert.butyl-phenyl)-2,3-dimethyl-allyl bromide and 3-methyl-piperidine there is obtained 1-[3-(p-tert.butyl-phenyl)-2,3-dimethyl-2-propenyl]-3-methyl-piperidine of boiling point 130° C./0.04 Torr, and from 3-(p-tert.butyl-phenyl)-2,3-dimethyl-allyl bromide and 3,5-dimethyl-piperidine there is obtained 1-[3-(p-tert.butyl-phenyl)-2,3-dimethyl-2-propenyl]-3,5-dimethyl-piperidine of boiling point 125° C./0.05 Torr.

EXAMPLE 16

Preparation of 1-[3-(p-tert.-butyl-phenyl)-2-methyl-propyl]-piperidine

To a solution of 4.5 g of 1-[3-(p-tert.butyl-phenyl)-2-methyl-2-propenyl]-piperidine in 125 ml of alcohol are added 1.7 ml of 32% hydrochloric acid and subsequently 1.5 g of 5% palladium/carbon and the mixture is then hydrogenated. After completion of the hydrogen uptake, the catalyst is filtered, the filtrate is treated with 200 ml of 10% sodium hydroxide and extracted with ether. The combined ether extracts are washed neutral with water, dried and evaporated. By distillation there is obtained pure 1-[3-(p-tert.butyl-phenyl)-2-methyl-propyl]-piperidine of boiling point 104° C./0.032 Torr.

In an analogous manner, from 4-[3-(4-tert.butyl-cyclohexyl)-2-methyl-2-propenyl]-2,6-dimethyl-morpholine there is obtained 4-[3-(4-tert.butyl-cyclohexyl)-2-methyl-propyl]-2,6-dimethyl-morpholine of boiling point 107°-110° C./0.01 Torr, from 1-[3-(p-tert.butyl-phenyl)-2,3-dimethyl-2-propenyl]-piperidine there is obtained 1-[3-(p-tert.butyl-phenyl)-2,3-dimethyl-propyl]-piperidine of boiling point 100°-104° C./0.03 Torr, from 1-[3-(p-tert.butyl-phenyl)-2,3-dimethyl-2-propenyl]-3-methyl-piperidine there is obtained 1-[3-(p-tert.butyl-phenyl)-2,3-dimethyl-propyl]-3-methyl-piperidine of boiling point 110° C./0.04 Torr, from 1-[3-(p-tert.butyl-phenyl)-2,3-dimethyl-2-propenyl]-3,5-dimethyl-piperidine there is obtained 1-[3-(p-tert.butyl-phenyl)-2,3-dimethyl-propyl]-3,5-dimethyl-piperidine of boiling point 114° C./0.04 Torr, from 4-[3-(p-tert.butyl-phenyl)-2,3-dimethyl-2-propenyl]-2,6-dimethyl-morpholine there is obtained 4-[3-(p-tert.butyl-phenyl)-2,3-dimethyl-propyl]-2,6-dimethyl-morpholine of boiling point 138°-142° C./0.03 Torr, and from 1-[3-(p-tert.butyl-phenyl)-1,2,3-trimethyl-2-propenyl]-piperidine there is obtained 1-[3-(p-tert.butyl-phenyl)-1,2,3-trimethyl-propyl]-piperidine of boiling point 147°-150° C./0.03 Torr.

EXAMPLE 17

Preparation of 1-[3-(4-tert.-butyl-cyclohexyl)-2-methyl-propyl]-piperidine 7 g of platinum dioxide and 7 g of active carbon are suspended in 500 ml of glacial acetic acid and prehydrogenated. Subsequently, a solution of 36.8 g of 1-[3-(p-tert.butyl-phenyl)-2-methyl-propyl]-piperidine in 1000 ml of glacial acetic acid and 67 ml of perchloric acid is added and the mixture is hydrogenated at 25° C. The catalyst is removed by filtration and the filtrate is treated with 110 g of potassium acetate dissolved in 100 ml of water. The precipitated potassium perchlorate is filtered, and the filtrate is evaporated on a rotary evaporator. The crystalline residue is made alkaline with 2-N sodium hydroxide, the free base is extracted with 500 ml of ether, washed neutral with water, dried over sodium sulphate and evaporated. By distillation there is obtained pure 1-[3-(4-tert.butyl-cyclohexyl)-2-methyl-propyl]-piperidine of boiling point 102° C./0.02 Torr.

In an analogous manner, from 1-[3-(p-tert.butyl-phenyl)-2-methyl-propyl]-3-methyl-piperidine there is obtained 1-[3-(4-tert.butyl-cyclohexyl)-2-methyl-propyl]-3-methyl-piperidine of boiling point 98° C./0.01 Torr, from 1-[3-(p-tert.butyl-phenyl)-2-methyl-propyl]-3-ethyl-piperidine there is obtained 1-[3-(4-tert.butyl-cyclohexyl)-2-methyl-propyl]-3-ethyl-piperidine of boiling point 125°–127° C./0.004 Torr, from 1-[3-(p-tert.butyl-phenyl)-2-methyl-propyl]-3,5-dimethyl-piperidine there is obtained 1-[3-(4-tert.butyl-cyclohexyl)-2-methyl-propyl]-3,5-dimethyl-piperidine of boiling point 115°–117° C./0.005 Torr, from 1-[3-(p-tert.butyl-phenyl)-2-methyl-propyl]-3,4-dimethyl-piperidine there is obtained 1-[3-(4-tert.butyl-cyclohexyl)-2-methyl-propyl]-3,4-dimethyl-piperidine of boiling point 122°–124° C./0.02 Torr, and from 1-[3-(p-tert.butyl-phenyl)-2-methyl-propyl]-3-ethyl-4-methyl-piperidine there is obtained 1-[3-(4-tert.butyl-cyclohexyl)-2-methyl-propyl]-3-ethyl-4-methyl-piperidine of boiling point 118°–121° C./0.001 Torr.

EXAMPLE 18

Preparation of 4-[3-(p-tert.butyl-phenyl)-2-methyl-propyl]-2,6-dimethyl-morpholine 4-oxide A solution of 120 ml of acetic anhydride and 120 ml of 30% hydrogen peroxide is added dropwise to 40 g of 4-[3-(p-tert.-butyl-phenyl)-2-methyl-propyl]-2,6-dimethyl-morpholine while cooling with an ice-bath so that the temperature does not exceed 45°–50° C. After stirring at room temperature for 16 hours, the mixture is cooled to −10° C. and treated with 280 ml of 40% potassium hydroxide solution, exhaustively extracted with chloroform and concentrated in vacuo at 30° C. (bath temperature). The residue is stirred at room temperature with 2-N sodium hydroxide solution for 16 hours and again extracted several times with chloroform. The combined chloroform extracts are washed neutral with sodium chloride solution, dried over sodium sulphate and evaporated. The highly viscous, syrupy residue is crystallised from ether/pentane. There is obtained pure 4-[3-(p-tert.butyl-phenyl)-2-methyl-propyl]-2,6-dimethyl-morpholine-4-oxide in the form of the hydrate; melting point 115°–118° C.

In an analogous manner, from 1-[3-(p-tert.butyl-phenyl)-2-methyl-propyl]-3,5-dimethyl-piperidine there is obtained 1-[3-(p-tert.butyl-phenyl)-2-methyl-propyl]-3,5-dimethyl-piperidine-1-oxide of melting point 79°–84° C. (hydrate), from 1-[3-(p-tert.butyl-phenyl)-2-methyl-propyl]-3,3-dimethyl-piperidine there is obtained 1-[3-(p-tert.butyl-phenyl)-2-methyl-propyl]-3,3-dimethyl-piperidine-1-oxide of melting point 73°–80° C. (hydrate), from 1-[3-(p-tert.butyl-phenyl)-2-methyl-propyl]-piperidine there is obtained 1-[3-(p-tert.butyl-phenyl)-2-methyl-propyl]-piperidine-1-oxide of melting point 83°–85° C. (hydrate), from 1-[3-(p-tert.butyl-phenyl)-2-methyl-propyl]-3-methyl-piperidine there is obtained 1-[3-(p-tert.butyl-phenyl)-2-methyl-propyl]-3-methyl-piperidine-1-oxide of melting point 80°–84° C. (hydrate), from 4-[3-(p-tert.butyl-phenyl)-2-methyl-propyl]-morpholine there is obtained 4-[3-(p-tert.butyl-phenyl)-2-methyl-propyl]-morpholine-4-oxide of melting point 85°–88° C. (hydrate), from 1-[3-(4-tert.butyl-cyclohexyl)-2-methyl-propyl]-piperidine there is obtained 1-[3-(4-tert.butyl-cyclohexyl)-2-methyl-propyl]-piperidine-1-oxide of melting point 130°–133° C., from 1-[3-(p-tert.butyl-phenyl)-2-methyl-propyl]-2,4-dimethyl-piperidine there is obtained 1-[3-(p-tert.butyl-phenyl)-2-methyl-propyl]-2,4-dimethyl-piperidine-1-oxide of melting point 103°–112° C. (hydrate), from 1-[3-(p-tert.butyl-phenyl)-2-methyl-propyl]-2,5-dimethyl-piperidine there is obtained 1-[3-(p-tert.butyl-phenyl)-2-methyl-propyl]-2,5-dimethyl-piperidine-1-oxide of melting point 91°–107° C. (hydrate), from 1-[3-(p-tert.butyl-phenyl)-2-methyl-propyl]-3,5-dimethyl-piperidine there is obtained 1-[3-(p-tert.butyl-phenyl)-2-methyl-propyl]-3,5-dimethyl-piperidine-1-oxide of melting point 79°–84° C. (hydrate), from 1-[3-(p-tert.butyl-phenyl)-2-methyl-propyl]-3,4-dimethyl-piperidine there is obtained 1-[3-(p-tert.butyl-phenyl)-2-methyl-propyl]-3,4-dimethyl-piperidine-1-oxide of melting point 80°–89° C. (hydrate), from 1-[3-(p-tert.butyl-phenyl)-2-methyl-propyl]-3-ethyl-piperidine there is obtained 1-[3-(p-tert.butyl-phenyl)-2-methyl-propyl]-3-ethyl-piperidine-1-oxide of melting point 118°–125° C. (hydrate), from 1-[3-(p-tert.butyl-phenyl)-2-methyl-propyl]-3-ethyl-4-methyl-piperidine there is obtained 1-[3-(p-tert.butyl-phenyl)-2-methyl-propyl]-3-ethyl-4-methyl-piperidine-1-oxide of melting point 115°–129° C. (hydrate), from 1-[3-(p-tert.butyl-phenyl)-2-methyl-propyl]-2,4,6-trimethyl-piperidine there is obtained 1-[3-(p-tert.butyl-phenyl)-2-methyl-propyl]-2,4,6-trimethyl-piperidine-1-oxide of melting point 101°–110° C. (hydrate), from 1-[3-(p-tert.butyl-phenyl)-2-methyl-propyl]-3,3-dimethyl-piperidine there is obtained 1-[3-(p-tert.butyl-phenyl)-2-methyl-propyl]-3,3-dimethyl-piperidine-1-oxide of melting point 73°–80° C. (hydrate), from 1-[3-(4-tert.butyl-cyclohexyl)-2-methyl-propyl]-3-ethyl-piperidine there is obtained 1-[3-(4-tert.butyl-cyclohexyl)-2-methyl-propyl]-3-ethyl-piperidine-1-oxide; $n_D^{20} = 1.4911$ (hydrate), from 1-[3-(4-tert.butyl-cyclohexyl)-2-methyl-propyl]-3,4-dimethyl-piperidine there is obtained 1-[3-(4-tert.butyl-cyclohexyl)-2-methyl-propyl]-3,4-dimethyl-piperidine-1-oxide; $n_D^{20} = 1.4899$ (hydrate), from 1-[3-(4-tert.butyl-cyclohexyl)-2-methyl-propyl]-3,5-dimethyl-piperidine there is obtained 1-[3-(4-tert.butyl-cyclohexyl)-2-methyl-propyl]-3,5-dimethyl-piperidine-1-oxide; $n_D^{20} = 1.488$ (hydrate), and from 4-[3-(4-tert.butyl-cyclohexyl)-2-methyl-propyl]-2,6-dimethyl-morpholine there is obtained 4-[3-(4-tert.-butyl-cyclohexyl)-2-methyl-propyl]-2,6-dimethyl-morpholine-4-oxide; $n_D^{20} = 1.4906$.

EXAMPLE 19

Preparation of 1-[3-(p-tert.-butyl-phenyl)-2-methyl-2-propenyl]-piperidine 1 oxide 5.4 g of 30% hydrogen peroxide are added dropwise at 40° C. to a solution of 5.4 g of 1-[3-(p-tert.butyl-phenyl)-2-methyl-2-propenyl]-piperidine in 40 ml of isopropanol, this addition being repeated after 24 hours. After stirring at 40° C. for 60 hours, the mixture is cooled and the excess hydrogen peroxide is decomposed by the addition of platinum sponge. The solution is filtered, the filtrate is evaporated, the residue is taken up in 50 ml of water and extracted with hexane. The aqueous solution is subsequently evaporated and the residue is crystallised from pentane. There is obtained pure 1-[3-(p-tert.butyl-phenyl)-2-methyl-2-propenyl]-piperidine-1-oxide of melting point 82°-88° C. (hydrate).

In an analogous manner, from 1-[3-(4-tert.butyl-cyclohexyl)-2-methyl-2-propenyl]-3-methyl-piperidine there is obtained 1-[3-(4-tert.butyl-cyclohexyl)-2-methyl-2-propenyl]-3-methyl-piperidine-1-oxide (hydrate) in the form of a viscous oil; $n_D^{20} = 1.4931$ (unsharp), and from 4-[3-(p-tert.butyl-phenyl)-2-methyl-2-propenyl]-2,6-dimethyl-morpholine there is obtained 4-[3-(p-tert.butyl-phenyl)-2-methyl-2-propenyl]-2,6-dimethyl-morpholine-4-oxide of melting point 99°-101° C. (hydrate).

The following Examples illustrate the preparation of the starting materials:

EXAMPLE 20

Preparation of 3-(p-tert.-butyl-phenyl)-2-methyl-acrolein 108.5 g of p-tert.butyl-benzaldehyde are added under nitrogen gasification to a solution of 1.4 g of potassium hydroxide in 100 ml of methanol and 39.2 g of propionaldehyde are subsequently added dropwise at 40° C. over a period of 6 hours. Subsequently, the mixture is further stirred at 40° C. for 1 hour, 1.5 ml of acetic acid are added and the mixture is concentrated on a rotary evaporator. The oily suspension is taken up in ether, washed neutral with water, dried and evaporated. By distillation there is obtained pure 3-(p-tert.butyl-phenyl)-2-methyl-acrolein of boiling point 165° C./11 Torr.

EXAMPLE 21

Preparation of 4-(p-tert.-butyl-phenyl)-3-methyl-3-buten-2-one 300 g of 32% hydrochloric acid are added dropwise at 15°-20° C. over a period of 1 hour to a mixture of 300 g of p-tert.-butyl-benzaldehyde and 300 g of methyl ethyl ketone and the mixture is left to stir at room temperature for 22 hours. Subsequently, the mixture is taken up in 200 ml of ether, washed with water and saturated sodium bicarbonate solution, dried over sodium sulphate and concentrated. By fractional distillation there is obtained pure 4-(p-tert.butyl-phenyl)-3-methyl-3-buten-2-one of boiling point 120° C./0.03 Torr.

EXAMPLE 22

Preparation of 3-(p-tert.-butyl-phenyl)-2-methyl-allyl alcohol 404.5 g of 3-(p-tert.butyl-phenyl)-2-methyl-acrolein are dissolved in 2500 ml of methanol and treated portionwise with 38 g of sodium borohydride while cooling with ice. Subsequently, the mixture is stirred at room temperature for 2.5 hours, poured into 2500 ml of ice-cold 2-N hydrochloric acid and exhaustively extracted with hexane. The combined hexane extracts are washed neutral with water, dried over sodium sulphate and evaporated. Vacuum distillation yields pure 3-(p-tert.-butyl-phenyl)-2-methyl-allyl alcohol of boiling point 119° C./0.005 Torr.

3-(p-Tert.butyl-phenyl)-1,2-dimethyl-allyl alcohol of boiling point 107° C./0.005 Torr can be prepared in an analogous manner from 4-(p-tert.butyl-phenyl)-3-methyl-3-buten-2-one.

EXAMPLE 23

Preparation of 3-(p-tert.-butyl-phenyl)-2-methyl-allyl bromide 73.2 g of 3-(p-tert.butyl-phenyl)-2-methyl-allyl alcohol nd 8.6 ml of pyridine in 700 ml of n-pentane are cooled down to −5° C. At this temperature there are added dropwise while stirring over a period of 2 hours 15.2 ml of phosphorus tribromide in 700 ml of n-pentane and the mixture is stirred at room temperature for 3 hours. The mixture is poured on to 500 g of ice and stirred up for 30 minutes. The pentane phase is separated and the aqueous phase is back-extracted with n-pentane. The combined n-pentane phases are washed neutral with saturated sodium bicarbonate solution and water, dried over sodium sulphate and evaporated. The 3-(p-tert.butyl-phenyl)-2-methyl-allyl bromide, distilled in a high vacuum, boils at 123° C./0.01 Torr.

It is to be noted that the substituted allyl bromides of formula IIa (see Formula Schemes A and B) are thermally unstable. In the distillation of these allyl bromides partial decomposition sets in. It is therefore advantageous to use the allyl bromides in the process provided by the present invention without purification.

In an analogous manner, from 3-(p-tert.butyl-phenyl)-1,2-dimethyl-allyl alcohol there is obtained 3-(p-tert.butyl-phenyl)-1,2-dimethyl-allyl bromide; $n_D^{20} = 1.5654$, from 3-(p-tert.butyl-phenyl)-2,3-dimethyl-allyl alcohol there is obtained 3-(p-tert.butyl-phenyl)-2,3-dimethyl-allyl bromide; $n_D^{20} = 1.5505$, from 3-(p-tert.butyl-phenyl)-1,2,3-trimethyl-allyl alcohol there is obtained 3-(p-tert.butyl-phenyl)-1,2,3-trimethyl-allyl bromide; NMR (60 Mc, CDCl$_3$): CH-1 = 5.05 ppm (q), and from 3-(4-tert.butyl-cyclohexyl)-2-methyl-allyl alcohol there is obtained 3-(4-tert.butyl-cyclohexyl)-2-methyl-allyl bromide of boiling point 94°-98° C./0.05 Torr.

EXAMPLE 24

Preparation of 3-(4-tert.-butyl-cyclohexyl)-2-methyl-acrylic acid ethyl ester

A mixture of 20.2 g of 4-tert.butyl-cyclohexane-1-carboxaldehyde, 52 g of (α-carbethoxy-ethylidene)-triphenyl-phosphorane and 3.6 g of benzoic acid in 120 ml of toluene is heated at reflux for 16 hours under nitrogen gasification and the toluene is evaported. The oily-crystalline residue is dissolved in 600 ml of methanol/water (4:1) and exhaustively extracted with hexane. The combined hexane extracts are washed with sodium bicarbonate solution and water, dried over sodium sulphate and evaporated. By distillation there is obtained pure 3-(4-tert.butyl-cyclohexyl)-2-methyl-acrylic acid ethyl ester of boiling point 99° C./0.03 Torr.

EXAMPLE 25

Preparation of 3-(p-tert.-butyl-phenyl)-2,3-dimethyl-acrylic acid ethyl ester 285.8 g of triethyl-α-phosphonium propionate are added to a solution of 27.6 g of sodium in 1.1 liters of absolute ethanol. After stirring for 5 minutes, 176.3 g of p-tert.butyl-acetophenone are added dropwise within 15 minutes and the mixture is stirred at reflux for 24 hours. Thereafter, the solution is cooled, stirred up with 4.4 liters of water and extracted with chloroform. The combined chloroform extracts are washed with water, dried over sodium sulphate and concentrated. By distillation there is obtained pure 3-(p-tert.butyl-phenyl)-2,3-dimethyl-acrylic acid ethyl ester of boiling point 99° C./0.005 Torr.

EXAMPLE 26

Preparation of p-tert.-butyl-α,β-dimethyl-cinnamaldehyde

A solution of 270 ml of morpholine in 1000 ml of absolute toluene is added dropwise at 0° C. over a period of 30-40 minutes to 740 ml of a 70% sodium dihydro-bis(2-methoxyethoxy)-aluminate solution in toluene and 1200 ml of toluene. The resulting solution is added dropwise at 0° C. over a period of 1 hour to 78.0 g of 3-(p-tert.butyl-phenyl)-2,3-dimethyl-acrylic acid ethyl ester in 340 ml of absolute toluene. The mixture is then stirred at 0° C. for 0.75 hour, poured into 3 liters of water and hydrochloric acid is added until the emulsion is eliminated. The toluene solution is separated, washed with water and sodium bicarbonate solution, dried over sodium sulphate and concentrated. By distillation there is obtained pure p-tert.butyl-α,β-dimethyl-cinnamaldehyde of boiling point 122°-128° C./0.005 Torr.

EXAMPLE 27

Preparation of 3-(p-tert.-butyl-phenyl)-1,2,3-trimethyl-allyl alcohol

A Grignard solution is prepared in the usual manner from 10.7 g of magnesium in 30 ml of absolute ether and 68.8 g of methyl iodide in 100 ml of absolute ether. To this solution are added dropwise at 20°-25° C. over a period of 15-20 minutes 56.1 g of p-tert.butyl-α,β-dimethyl-cinnamaldehyde. After cooling to room temperature, the mixture is cautiously poured on to 200 g of ice and 150 g of technical ammonium chloride in 500 ml of water are added. The organic phase is separated, washed with water and sodium bicarbonate solution, dried over sodium sulphate and concentrated. By distillation there is obtained pure 3-(p-tert.butyl-phenyl)-1,2,3-trimethyl-allyl alcohol of boiling point 143°-148° C./0.001 Torr.

EXAMPLE 28

Preparation of 3-(4-tert.-butyl-cyclohexyl)-2-methyl-allyl alcohol 46 g. of a 70% sodium dihydro-bis(2-methoxyethoxy)-aluminate solution in toluene are added dropwise at 25°-30° C. over a period of 90 minutes to a solution of 25.3 g of 3-(4-tert.butyl-cyclohexyl)-2-methyl-acrylic acid ethyl ester in 130 ml of absolute toluene and the mixture is subsequently warmed at 40° C. for 2 hours. The mixture is then cooled down to −10° C., treated dropwise with 130 ml of 2-N sodium hydroxide, the toluene phase is separated and the aqueous-alkaline phase is back-extracted twice with 200 ml of toluene. The combined toluene phases are washed neutral with water, dried over sodium sulphate and evaporated. By distillation there is obtained pure 3-(4-tert.butyl-cyclohexyl)-2-methyl-allyl alcohol of boiling point 112°-114° C./0.08 Torr.

3-(p-Tert.butyl-phenyl)-2,3-dimethyl-allyl alcohol of boiling point 107°-110° C./0.005 Torr can be obtained in an analogous manner from 3-(p-tert.butyl-phenyl)-2,3-dimethyl-acrylic acid ethyl ester.

EXAMPLE 29

Preparation of 3-(p-tert.-butyl-phenyl)-2-methyl-propionaldehyde 72.8 g of 3-(p-tert.butyl-phenyl)-2-methyl-acrolein, 3.3 g of 5% palladium/carbon and 0.277 g of calcium hydroxide are flushed with nitrogen and added to a mixture of 5.3 ml of water and 198 ml of methanol. This mixture is hydrogenated at room temperature until 1 mol of hydrogen has been taken up. The catalyst is filtered, the filtrate is evaporated and the residue is distilled. There is obtained pure 3-(p-tert.butyl-phenyl)-2-methyl-propionaldehyde of boiling point 150° C./10 Torr.

EXAMPLE 30

Preparation of 1-[3-(p-tert.-butyl-phenyl)-2-methyl-1-propenyl]-piperidine 6.54 kg of 3-(p-tert.butyl-phenyl)-2-methyl-propionaldehyde and 3 kg of piperidine are heated at reflux overnight in 4.54 liters of toluene in a water-separator under nitrogen gasification and the toluene is distilled in vacuo. The residue is distilled in vacuo. There is obtained pure 1-[3-(p-tert.butyl-phenyl)-2-methyl-1-propenyl]-piperidine of boiling point 118°-120° C./0.026 Torr.

In an analogous manner,
from 3-(p-tert.butyl-phenyl)-2-methyl-propionaldehyde and 3-methyl-piperidine there is obtained 1-[3-(p-tert.butyl-phenyl)-2-methyl-1-propenyl]-3-methyl-piperidine of boiling point 123°-124° C./0.03 Torr,
from 3-(p-tert.butyl-phenyl)-2-methyl-propionaldehyde and morpholine there is obtained 4-[3-(p-tert.butyl-phenyl)-2-methyl-1-propenyl]-morpholine of boiling point 110°-114° C./0.05 Torr, and
from 3-(p-tert.butyl-phenyl)-2-methyl-propionaldehyde and 2,6-dimethyl-morpholine there is obtained 4-[3-(p-tert.butyl-phenyl)-2-methyl-1-propenyl]-2,6-dimethyl-morpholine of boiling point 127°-129° C./0.025 Torr.

The isolation of the enamines, as recognized by one skilled in the art, is only carried out in exceptional cases. In general, the enamines are reduced directly with formic acid (as described in Example 12) or hydrogenated in toluene solution without working-up (as described in Example 13).

EXAMPLE 31

Preparation of 3-(p-tert.-butyl-phenyl)-1,2-dimethyl-propanol 65 g of 3-(p-tert.butyl-phenyl)-1,2-dimethyl-allyl alcohol are dissolved in 650 ml of alcohol and treated with 6 g of 5% palladium/carbon while gassing with nitrogen. The mixture is hydrogenated until the hydrogen uptake has been completed. Subsequently, the catalyst is removed by filtration and the alcohol filtrate is evaporated. By distillation there is obtained pure 3-(p-tert.butyl-phenyl)-1,2-dimethyl-propanol of boiling point 110° C./0.03 Torr.

In an analogous manner,
from 3-(p-tert.butyl-phenyl)-2-methyl-allyl alcohol there is obtained 3-(p-tert.butyl-phenyl)-2-methyl-propanol of boiling point 148°–150° C./10 Torr,
from 3-(p-tert.butyl-phenyl)-2,3-dimethyl-allyl alcohol there is obtained 3-(p-tert.butyl-phenyl)-2,3-dimethyl-propanol, and
from 3-(p-tert.butyl-phenyl)-1,2,3-trimethyl-allyl alcohol there is obtained 3-(p-tert.butyl-phenyl)-1,2,3-trimethyl-propanol.

EXAMPLE 32

Preparation of 3-(p-tert.-butyl-phenyl)-2-methyl-propyl bromide 300.2 g of 3-(p-tert.butyl-phenyl)-2-methyl-propanol are added dropwise over a period of 2 hours at 20°–30° C. to 218.6 g of phosphorus tribromide and the mixture is left to stand for 16 hours. The mixture is subsequently heated to 55°–60° C. over a period of 1.5 hours, cooled to ca 10° C. and cautiously poured on to ice. The aqueous solution is exhaustively extracted with ether, the combined ether phases are washed with saturated sodium bicarbonate solution and water, dried over sodium sulphate and evaporated. By fraction distillation there is obtained pure 3-(p-tert.butyl-phenyl)-2-methyl-propyl bromide of boiling point 104° C./0.025 Torr.

In an analogous manner,
from 3-(p-tert.butyl-phenyl)-1,2-dimethyl-propanol there is obtained 3-(p-tert.butyl-phenyl)-1,2-dimethyl-propyl bromide of boiling point 112° C./0.05 Torr,
from 3-(p-tert.butyl-phenyl)-2,3-dimethyl-propanol there is obtained 3-(p-tert.butyl-phenyl)-2,3-dimethyl-propyl bromide, and
from 3-(p-tert.butyl-phenyl)-1,2,3-trimethyl-propanol there is obtained 3-(p-tert.butyl-phenyl)-1,2,3-trimethyl-propyl bromide.

III. PHARMACEUTICAL PREPARATIONS:

1. Vaginal tablets

EXAMPLE 33

Vaginal tablets can contain the following ingredients:

| Active ingredient (given in Table III) | 100 mg | 50 mg |
|---|---|---|
| Secondary calcium phosphate dihydrate | 300 mg | 400.0 mg |
| Directly pressable starch | 203 mg | 261.5 mg |
| Lactose (spray-dried) | 100 mg | 400.0 mg |
| Polyvinylpyrrolidone K 90 | 30 mg | 25.0 mg |
| Citric acid (anhydrous) | 5 mg | 5.0 mg |
| Magnesium stearate | 7 mg | 6.0 mg |
| | 745 mg | 695.0 mg |

2. Salves

EXAMPLE 34

A salve for topical application can contain the following ingredients:

| | |
|---|---|
| Active ingredient (given in Table III) | 1.00 g |
| Cetyl alcohol | 3.60 g |
| Lanolin | 9.00 g |
| Petroleum jelly (white) | 79.00 g |
| Paraffin oil | 7.40 g |
| | 100.00 g |

3. Creams

EXAMPLE 35

A cream for topical application can contain the following ingredients:

| | |
|---|---|
| Active ingredient (given in Table III) | 1.00 g. |
| Polyoxyethylene stearate | 3.00 g. |
| Stearyl alcohol | 8.00 g. |
| Paraffin oil, intensively viscous | 10.00 g. |
| Petroleum jelly (white) | 10.00 g. |
| High molecular weight carboxyvinyl polymer | 0.30 g. |
| NaOH pure | 0.07 g. |
| Water, deionized ad | 100.00 g. |

I claim
1. A compound of the formula

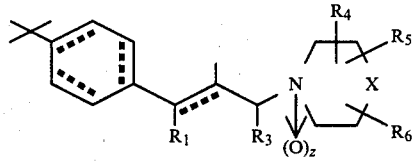

wherein $R_1$ and $R_3$, independently, are hydrogen or methyl;
$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; X is a methylene or an oxygen atom; z is zero or 1; and the dotted bonds can be hydrogenated,
or an acid addition salt of a compound thereof which is basic.

2. A compound of the formula

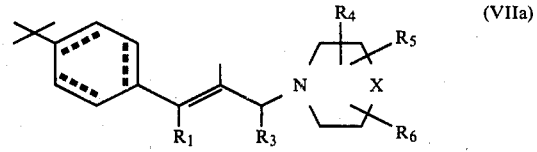

wherein $R_1$ and $R_3$, independently, are hydrogen or methyl;
$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; X is a methylene or an oxygen atom; and the dotted bonds can be hydrogenated, or an acid addition salt of a compound thereof which is basic.

3. A compound of the formula

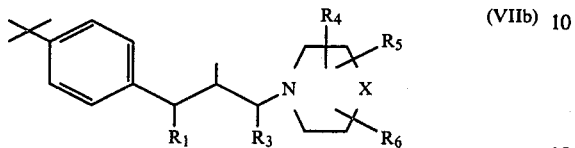 (VIIb)

, wherein $R_1$ and $R_3$, independently, are hydrogen or methyl;

$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; and X is a methylene or an oxygen atom;

or an acid addition salt of a compound fthereof which is basic.

4. A compound of the formula

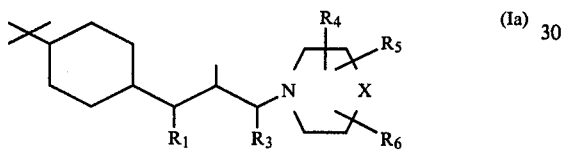 (Ia)

wherein $R_1$ and $R_3$, independently, are hydrogen or methyl;

$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; and X is a methylene or an oxygen atom;

or an acid addition salt of a compound thereof which is basic.

5. A compound of the formula

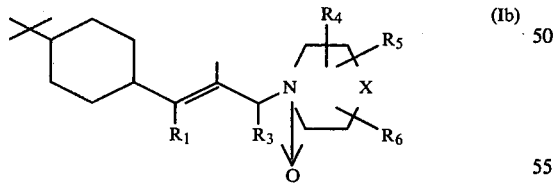 (Ib)

wherein $R_1$ and $R_3$, independently, are hydrogen or methyl;

$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; and X is a methylene or an oxygen atom;

or an acid addition salt of a compound thereof which is basic.

6. A compound of the formula

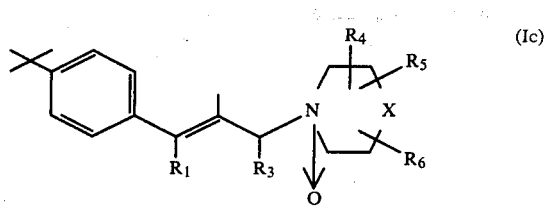 (Ic)

wherein $R_1$ and $R_3$, independently, are hydrogen or methyl;

$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; and X is a methylene or an oxygen atom;

or an acid addition salt of a compound thereof which is basic.

7. A compound of the formula

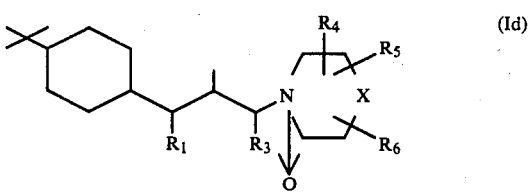 (Id)

wherein $R_1$ and $R_3$, independently, are hydrogen or methyl;

$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; and X is a methylene or an oxygen atom;

or an acid addition salt of a compound thereof which is basic.

8. A compound of the formula

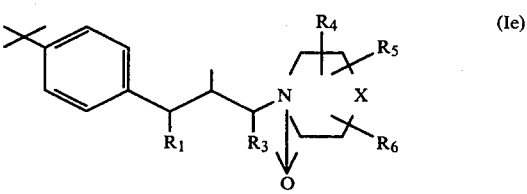 (Ie)

wherein $R_1$ and $R_3$, independently, are hydrogen or methyl;

$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; and X is a methylene or an oxygen atom;

or an acid addition salt of a compound thereof which is basic.

9. A compound of the formula

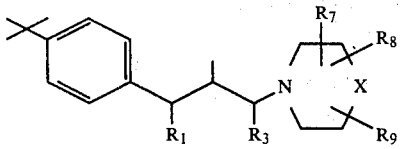

wherein $R_1$ and $R_3$, independently, are hydrogen or methyl;

$R_7$, $R_8$ and $R_9$, independently, are hydrogen or methyl; and X is methylene or an oxygen atom, or an acid addition salt of a compound thereof which is basic.

10. A compound in accordance with claim 1, 1-[3-(p-Tert.butyl-phenyl)-2-methyl-propyl]-piperidine.

11. A compound in accordance with claim 1, 1-[3-(p-Tert.butyl-phenyl)-2-methyl-propyl]-3-methyl-piperidine.

12. A compound in accordance with claim 1, 4-[3-(p-Tert.butyl-phenyl)-2-methyl-propyl]-morpholine.

13. A compound in accordance with claim 1, 4-[3-(p-Tert.butyl-phenyl)-2-methyl-propyl]-2,6-dimethyl-morpholine.

14. A compound in accordance with claim 1, 1-[3-(p-Tert.butyl-phenyl)-2-methyl-propyl]-decahydroquinoline.

15. A compound in accordance with claim 1, 2-[3-(p-Tert.butyl-phenyl)-2-methyl-propyl]-1,2,3,4-tetrahydroisoquinoline.

16. A compound in accordance with claim 1, 1-[3-(p-Tert.butyl-phenyl)-2-methyl-propyl]-3,5-dimethyl-piperidine-1-oxide.

17. A compound in accordance with claim 1, 1-[3-(p-Tert.butyl-phenyl)-2-methyl-propyl]-2,4-dimethyl-piperidine-1-oxide.

18. A compound in accordance with claim 1, 1-[3-(p-Tert.butyl-phenyl)-2-methyl-propyl]-2,5-dimethyl-piperidine-1-oxide.

19. A compound in accordance with claim 1, 1-[3-(p-Tert.butyl-phenyl)-2-methyl-propyl]-3,5-dimethyl-piperidine-1-oxide.

20. A compound in accordance with claim 1, 1-[3-(p-Tert.butyl-phenyl)-2-methyl-propyl]-3,4-dimethyl-piperidine-1-oxide.

21. A compound in accordance with claim 1, 1-[3-(p-Tert.butyl-phenyl)-2-methyl-propyl]-3-ethyl-piperidine-1-oxide.

22. A compound in accordance with claim 1, 1-[3-(p-Tert.butyl-phenyl)-2-methyl-propyl]-3-ethyl-4-methyl-piperidine-1-oxide.

23. A compound in accordance with claim 1, 1-[3-(p-Tert.butyl-phenyl)-2-methyl-propyl]-2,4,6-trimethyl-piperidine-1-oxide.

24. A compound in accordance with claim 1, 1-[3-(p-Tert.butyl-phenyl)-2-methyl-propyl]-3,3-dimethyl-piperidine-1-oxide.

25. A compound in accordance with claim 1, 1-[3-(p-Tert.butyl-phenyl)-2-methyl-2-propenyl]-2-ethyl-piperidine.

26. A compound in accordance with claim 1, 1-[3-(p-Tert.butyl-phenyl)-2-methyl-2-propenyl]-3-methyl-piperidine.

27. A compound in accordance with claim 1, 1-[3-(p-Tert.butyl-phenyl)-2-methyl-2-propenyl]-3-ethyl-piperidine.

28. A compound in accordance with claim 1, 1-[3-(p-Tert.butyl-phenyl)-2-methyl-2-propenyl]-2,6-dimethyl-piperidine.

29. A compound in accordance with claim 1, 1-[3-(p-Tert.butyl-phenyl)-2-methyl-2-propenyl]-2,4-dimethyl-piperidine.

30. A compound in accordance with claim 1, 1-[3-(p-Tert.butyl-phenyl)-2-methyl-2-propenyl]-2,5-dimethyl-piperidine.

31. A compound in accordance with claim 1, 1-[3-(p-Tert.butyl-phenyl)-2-methyl-2-propenyl]-5-ethyl-2-methyl-piperidine.

32. A compound in accordance with claim 1, 1-[3-(p-Tert.butyl-phenyl)-2-methyl-2-propenyl]-3,5-dimethyl-piperidine.

33. A compound in accordance with claim 1, 1-[3-(p-Tert.butyl-phenyl)-2-methyl-propyl]-2-methyl-piperidine.

34. A compound in accordance with claim 1, 1-[3-(p-Tert.butyl-phenyl)-2-methyl-propyl]-4-methyl-piperidine.

35. A compound in accordance with claim 1, 1-[3-(p-Tert.butyl-phenyl)-2-methyl-propyl]-4-ethyl-piperidine.

36. A compound in accordance with claim 1, 1-[3-(p-Tert.butyl-phenyl)-2-methyl-propyl]-2,6-dimethyl-piperidine.

37. A compound in accordance with claim 1, 1-[3-(p-Tert.butyl-phenyl)-2-methyl-propyl]-1,2,3,4-tetrahydroquinoline.

38. A compound in accordance with claim 1, 1-[3-(p-Tert.butyl-phenyl)-2-methyl-2-propenyl]-4-ethyl-piperidine.

39. A compound in accordance with claim 1, 1-[3-(p-Tert.butyl-phenyl)-2-methyl-2-propenyl]-3,4-dimethyl-piperidine.

40. A compound in accordance with claim 1, 1-[3-(p-Tert.butyl-phenyl)-2-methyl-2-propenyl]-3-ethyl-4-methyl-piperidine.

41. A compound in accordance with claim 1, 1-[3-(p-Tert.butyl-phenyl)-2-methyl-2-propenyl]-2,4,6-trimethyl-piperidine.

42. A compound in accordance with claim 1, 1-[3-(p-Tert.butyl-phenyl)-2-methyl-2-propenyl]-3,3-dimethyl-piperidine.

43. A compound in accordance with claim 1, 4-[3-(p-Tert.butyl-phenyl)-2-methyl-2-propenyl]-2,6-dimethyl-morpholine-4-oxide.

44. A compound in accordance with claim 1, 2-[3-(p-Tert.butyl-phenyl)-2-methyl-propyl]-decahydroquinoline.

45. A compound in accordance with claim 1, 4-[3-(p-Tert.butyl-phenyl)-2,3-dimethyl-2-propenyl]-2,6-dimethyl-morpholine.

46. A compound in accordance with claim 1, 1-[3-(p-Tert.butyl-phenyl)-2-methyl-propyl]-2-ethyl-piperidine.

47. A compound in accordance with claim 1, 1-[3-(p-Tert.butyl-phenyl)-2-methyl-propyl]-3-ethyl-piperidine.

48. A compound in accordance with claim 1, 1-[3-(p-Tert.butyl-phenyl)-2-methyl-propyl]-2,4-dimethyl-piperidine.

49. A compound in accordance with claim 1, 1-[3-(p-Tert.butyl-phenyl)-2-methyl-propyl]-2,5-dimethyl-piperidine.

50. A compound in accordance with claim 1, 1-[3-(p-Tert.butyl-phenyl)-2-methyl-propyl]-5-ethyl-2-methyl-piperidine.

51. A compound in accordance with claim 1, 1-[3-(p-Tert.butyl-phenyl)-2-methyl-propyl]-3,5-dimethyl-piperidine.

52. A compound in accordance with claim 1, 1-[3-(p-Tert.butyl-phenyl)-2-methyl-propyl]-3,4-dimethyl-piperidine.

53. A compound in accordance with claim 1, 1-[3-(p-Tert.butyl-phenyl)-2-methyl-propyl]-3-ethyl-4-methyl-piperidine.

54. A compound in accordance with claim 1, 1-[3-(p-Tert.butyl-phenyl)-2-methyl-propyl]-2,4,6-trimethyl-piperidine.

55. A compound in accordance with claim 1, 1-[3-(p-Tert.butyl-phenyl)-2-methyl-propyl]-3,3-dimethyl-piperidine.

56. A compound in accordance with claim 1, 1-[3-(p-Tert.butyl-phenyl)-2,3-dimethyl-propyl]-piperidine.

57. A compound in accordance with claim 1, 1-[3-(p-Tert.butyl-phenyl)-1,2-dimethyl-propyl]-piperidine.

58. A compound in accordance with claim 1, 1-[3-(p-Tert.butyl-phenyl)-2-methyl-2-propenyl]-piperidine.

59. A compound in accordance with claim 1, 4-[3-(p-Tert.butyl-phenyl)-2-methyl-2-propenyl]-2,6-dimethyl-morpholine.

60. A compound in accordance with claim 1, 1-[3-(p-Tert.butyl-phenyl)-2,3-dimethyl-2-propenyl]-piperidine.

61. A compound in accordance with claim 1, 1-[3-(4-Tert.butyl-cyclohexyl)-2-methyl-2-propenyl]-piperidine.

62. A compound in accordance with claim 1, 1-[3-(4-Tert.butyl-cyclohexyl)-2-methyl-2-propenyl]-3-methyl-piperidine.

63. A compound in accordance with claim 1, 4-[3-(4-Tert.butyl-cyclohexyl)-2-methyl-2-propenyl]-2,6-dimethyl-morpholine.

64. A compound in accordance with claim 1, 1-[3-(4-Tert.butyl-phenyl)-2-methyl-propyl]-3,3-dimethyl-piperidine-1-oxide.

65. A compound in accordance with claim 1, 4-[3-(4-Tert.butyl-cyclohexyl)-2-methyl-propyl]-2,6-dimethyl-morpholine.

66. A compound in accordance with claim 1, 1-[3-(4-Tert.butyl-cyclohexyl)-2-methyl-propyl]-piperidine.

67. A compound in accordance with claim 1, 1-[3-(4-Tert.butyl-cyclohexyl)-2-methyl-propyl]-3-methyl-piperidine.

68. A compound in accordance with claim 1, 4-[3-(p-Tert.butyl-phenyl)-2-methyl-propyl]-2,6-dimethyl-morpholine-4-oxide.

69. A compound in accordance with claim 1, 1-[3-(p-Tert.butyl-phenyl)-2-methyl-propyl]-piperidine-1-oxide.

70. A compound in accordance with claim 1, 1-[3-(p-Tert.butyl-phenyl)-2-methyl-propyl]-3-methyl-piperidine-1-oxide.

71. A compound in accordance with claim 1, 4-[3-(p-Tert.butyl-phenyl)-2-methyl-propyl]-morpholine-4-oxide.

72. A compound in accordance with claim 1, 1-[3-(p-Tert.butyl-phenyl)-1,2,3-trimethyl-2-propenyl]-piperidine.

73. A compound in accordance with claim 1, 1-[3-(p-Tert.butyl-phenyl)-1,2,3-trimethyl-propyl]-piperidine.

74. A compound in accordance with claim 1, 1-[3-(p-Tert.butyl-phenyl)-1,2-dimethyl-2-propenyl]-piperidine.

75. A compound in accordance with claim 1, 1-[3-(4-Tert.butyl-cyclohexyl)-2-methyl-propyl]-3-ethyl-piperidine.

76. A compound in accordance with claim 1, 1-[3-(4-Tert.butyl-cyclohexyl)-2-methyl-propyl]-3,5-dimethyl-piperidine.

77. A compound in accordance with claim 1, 1-[3-(4-Tert.butyl-cyclohexyl)-2-methyl-propyl]-3,4-dimethyl-piperidine.

78. A compound in accordance with claim 1, 1-[3-(4-Tert.butyl-cyclohexyl)-2-methyl-propyl]-3-ethyl-4-methyl-piperidine.

79. A compound in accordance with claim 1, 1-[3-(4-Tert.butyl-cyclohexyl)-2-methyl-propyl]-3-ethyl-piperidine-1-oxide.

80. A compound in accordance with claim 1, 1-[3-(4-Tert.butyl-cyclohexyl)-2-methyl-propyl]-3,4-dimethyl-piperidine-1-oxide.

81. A compound in accordance with claim 1, 1-[3-(4-Tert.butyl-cyclohexyl)-2-methyl-propyl]-3,5-dimethyl-piperidine-1-oxide.

82. A compound in accordance with claim 1, 4-[3-(4-Tert.butyl-cyclohexyl)-2-methyl-propyl]-2,6-dimethyl-morpholine-4-oxide.

83. A compound in accordance with claim 1, 1-[3-(4-Tert.butyl-cyclohexyl)-2-methyl-propyl]-piperidine-1-oxide.

84. A compound in accordance with claim 1, 1-[3-(p-Tert.butyl-phenyl)-2-methyl-2-propenyl]-piperidine-1-oxide.

85. A compound in accordance with claim 1, 1-[3-(4-Tert.butyl-cyclohexyl)-2-methyl-2-propenyl]-3-methyl-piperidine-1-oxide.

86. A compound in accordance with claim 1, 1-[3-(p-Tert.butyl-phenyl)-2,3-dimethyl-2-propenyl]-3-methyl-piperidine.

87. A compound in accordance with claim 1, 1-[3-(p-Tert.butyl-phenyl)-2,3-dimethyl-2-propenyl]-3,5-dimethyl-piperidine.

88. A compound in accordance with claim 1, 1-[3-(p-Tert.butyl-phenyl)-2,3-dimethyl-propyl]-3-methyl-piperidine.

89. A compound in accordance with claim 1, 1-[3-(p-Tert.butyl-phenyl)-2,3-dimethyl-propyl]-3,5-dimethyl-piperidine.

90. A compound in accordance with claim 1, 4-[3-(p-Tert.butyl-phenyl)-2,3-dimethyl-propyl]-2,6-dimethyl-morpholine.

91. A compound in accordance with claim 1, 1-[3-(4-Tert.butyl-cyclohexyl)-2-methyl-propyl]-3-methyl-piperidine-1-oxide.

92. A fungicidal composition comprising an effective amount of at least one compound of the formula

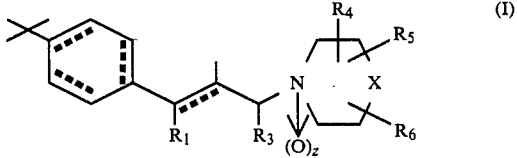

wherein $R_1$ and $R_3$, independently, are hydrogen or methyl;

$R_4$, $R_5$ and $R_6$, independently, are hydrogen or alkyl of 1 to 4 carbon atoms, and two of $R_4$, $R_5$ and $R_6$ can each be bonded to the same carbon atom or together can form a fused alicyclic or aromatic six-membered ring; X is a methylene or an oxygen atom; z is zero or 1; and the dotted bonds can be hydrogenated, or an acid addition salt of a compound thereof which is basic and an inert carrier material.

93. A fungicidal composition, in accordance with claim 92, which contains 1-[3-(p-tert.butyl-phenyl)-2-methyl-propyl]-piperidine.

94. A fungicidal composition, in accordance with claim 92, which contains 1-[3-(p-tert.butyl-phenyl)-2-methyl-propyl]-3-methyl-piperidine.

95. A fungicidal composition, in accordance with claim 92, which contains 4-[3-(p-tert.butyl-phenyl)-2-methyl-propyl]-morpholine.

96. A fungicidal composition, in accordance with claim 92, which contains 4-[3-(p-tert.butyl-phenyl)-2-methyl-propyl]-2,6-dimethyl-morpholine.

97. A fungicidal composition, in accordance with claim 92, which contains 1-[3-(p-tert.butyl-phenyl)-2-methyl-propyl]-decahydroquinoline.

98. A fungicidal composition, in accordance with claim 92, which contains 2-[3-(p-tert.butyl-phenyl)-2-methyl-propyl]-1,2,3,4-tetrahydroisoquinoline.

99. A fungicidal composition, in accordance with claim 92, which contains 1-[3-(p-tert.butyl-phenyl)-2-methyl-propyl]-3,5-dimethyl-piperidine-1-oxide.

100. A fungicidal composition, in accordance with claim 92, which contains 1-[3-(p-tert.butyl-phenyl)-2-methyl-propyl]-2,4-dimethyl-piperidine-1-oxide.

101. A fungicidal composition, in accordance with claim 92, which contains 1-[3-(p-tert.butyl-phenyl)-2-methyl-propyl]-2,5-dimethyl-piperidine-1-oxide.

102. A fungicidal composition, in accordance with claim 92, which contains 1-[3-(p-tert.butyl-phenyl)-2-methyl-propyl]-3,5-dimethyl-piperidine-1-oxide.

103. A fungicidal composition, in accordance with claim 92, which contains 1-[3-(p-tert.butyl-phenyl)-2-methyl-propyl]-3,4-dimethyl-piperidine-1-oxide.

104. A fungicidal composition, in accordance with claim 92, which contains 1-[3-(p-tert.butyl-phenyl)-2-methyl-propyl]-3-ethyl-piperidine-1-oxide.

105. A fungicidal composition, in accordance with claim 92, which contains 1-[3-(p-tert.butyl-phenyl)-2-methyl-propyl]-3-ethyl-4-methyl-piperidine-1-oxide.

106. A fungicidal composition, in accordance with claim 92, which contains 1-[3-(p-tert.butyl-phenyl)-2-methyl-propyl]-2,4,6-trimethyl-piperidine-1-oxide.

107. A fungicidal composition, in accordance with claim 92, which contains 1-[3-(p-tert.butyl-phenyl)-2-methyl-propyl]-3,3-dimethyl-piperidine-1-oxide.

108. A fungicidal composition, in accordance with claim 92, which contains 1-[3-(p-tert.butyl-phenyl)-2-methyl-2-propenyl]-2-ethyl-piperidine.

109. A fungicidal composition, in accordance with claim 92, which contains 1-[3-(p-tert.butyl-phenyl)-2-methyl-2-propenyl]-3-methyl-piperidine.

110. A fungicidal composition, in accordance with claim 92, which contains 1-[3-(p-tert.butyl-phenyl)-2-methyl-2-propenyl]-3-ethyl-piperidine.

111. A fungicidal composition, in accordance with claim 92, which contains 1-[3-(p-tert.butyl-phenyl)-2-methyl-2-propenyl]-2,6-dimethyl-piperidine.

112. A fungicidal composition, in accordance with claim 92, which contains 1-[3-(p-tert.butyl-phenyl)-2-methyl-2-propenyl]-2,4-dimethyl-piperidine.

113. A fungicidal composition, in accordance with claim 92, which contains 1-[3-(p-tert.butyl-phenyl)-2-methyl-2-propenyl-2,5-dimethyl-piperidine.

114. A fungicidal composition, in accordance with claim 92, which contains 1-[3-(p-tert.butyl-phenyl)-2-methyl-2-propenyl]-5-ethyl-2-methyl-piperidine.

115. A fungicidal composition, in accordance with claim 92, which contains 1-[3-(p-tert.butyl-phenyl)-2-methyl-2-propenyl]-3,5-dimethyl-piperidine.

116. A fungicidal composition, in accordance with claim 92, which contains 1-[3-(p-tert.butyl-phenyl)-2-methyl-propyl]-2-methyl-piperidine.

117. A fungicidal composition, in accordance with claim 92, which contains 1-[3-(p-tert.butyl-phenyl)-2-methyl-propyl]-4-methyl-piperidine.

118. A fungicidal composition, in accordance with claim 92, which contains 1-[3-(p-tert.butyl-phenyl)-2-methyl-propyl]-4-ethyl-piperidine.

119. A fungicidal composition, in accordance with claim 92, which contains 1-[3-(p-tert.butyl-phenyl)-2-methyl-propyl]-2,6-dimethyl-piperidine.

120. A fungicidal composition, in accordance with claim 92, which contains 1-[3-(p-tert.butyl-phenyl)-2-methyl-propyl]-1,2,3,4-tetrahydroquinoline.

121. A fungicidal composition, in accordance with claim 92, which contains 1-[3-(p-tert.butyl-phenyl)-2-methyl-2-propenyl]-4-ethyl-piperidine.

122. A fungicidal composition, in accordance with claim 92, which contains 1-[3-(p-tert.butyl-phenyl)-2-methyl-2-propenyl]-3,4-dimethyl-piperidine.

123. A fungicidal composition, in accordance with claim 92, which contains 1-[3-(p-tert.butyl-phenyl)-2-methyl-2-propenyl]-3-ethyl-4-methyl-piperidine.

124. A fungicidal composition, in accordance with claim 92, which contains 1-[3-(p-tert.butyl-phenyl)-2-methyl-2-propenyl]-2,4,6-trimethyl-piperidine.

125. A fungicidal composition, in accordance with claim 92, which contains 1-[3-(p-tert.butyl-phenyl)-2-methyl-2-propenyl]-3,3-dimethyl-piperidine.

126. A fungicidal composition, in accordance with claim 92, which contains 4-[3-(p-tert.butyl-phenyl)-2-methyl-2-propenyl]-2,6-dimethyl-morpholine-4-oxide.

127. A fungicidal composition, in accordance with claim 92, which contains 2-[3-(p-tert.butyl-phenyl)-2-methyl-propyl]-decahydroisoquinoline.

128. A fungicidal composition, in accordance with claim 92, which contains 4-[3-(p-tert.butyl-phenyl)-2,3-dimethyl-2-propenyl]-2,6-dimethyl-morpholine.

129. A fungicidal composition, in accordance with claim 92, which contains 1-[3-(p-tert.butyl-phenyl)-2-methyl-propyl]-2-ethyl-piperidine.

130. A fungicidal composition, in accordance with claim 92, which contains 1-[3-(p-tert.butyl-phenyl)-2-methyl-propyl]-3-ethyl-piperidine.

131. A fungicidal composition, in accordance with claim 92, which contains 1-[3-(p-tert.butyl-phenyl)-2-methyl-propyl]-2,4-dimethyl-piperidine.

132. A fungicidal composition, in accordance with claim 92, which contains 1-[3-(p-tert.butyl-phenyl)-2-methyl-propyl]-2,5-dimethyl-piperidine.

133. A fungicidal composition, in accordance with claim 92, which contains 1-[3-(p-tert.butyl-phenyl)-2-methyl-propyl]-5-ethyl-2-methyl-piperidine.

134. A fungicidal composition, in accordance with claim 92, which contains 1-[3-(p-tert.butyl-phenyl)-2-methyl-propyl]-3,5-dimethyl-piperidine.

135. A fungicidal composition, in accordance with claim 92, which contains 1-[3-(p-tert.butyl-phenyl)-2-methyl-propyl]-3,4-dimethyl-piperidine.

136. A fungicidal composition, in accordance with claim 92, which contains 1-[3-(p-tert.butyl-phenyl)-2-methyl-propyl]-3-ethyl-4-methyl-piperidine.

137. A fungicidal composition, in accordance with claim 92, which contains 1-[3-(p-tert.butyl-phenyl)-2-methyl-propyl]-2,4,6-trimethyl-piperidine.

138. A fungicidal composition, in accordance with claim 92, which contains 1-[3-(p-tert.butyl-phenyl)-2-methyl-propyl]-3,3-dimethyl-piperidine.

139. A fungicidal composition, in accordance with claim 92, which contains 1-[3-(p-tert.-butyl-phenyl)-2,2-dimethyl-propyl]-piperidine.

140. A fungicidal composition, in accordance with claim 92, which contains 1-[3-(p-tert.-butyl-phenyl)-1,2-dimethyl-propyl]-piperidine.

141. A fungicidal composition, in accordance with claim 92, which contains 1-[3-(p-tert.butyl-phenyl)-2-methyl-2-propenyl]-piperidine.

142. A fungicidal composition, in accordance with claim 92, which contains 4-[3-(p-tert.butyl-phenyl)-2-methyl-2-propenyl]-2,6-dimethyl-morpholine.

143. A fungicidal composition, in accordance with claim 92, which contains 1-[3-(p-tert.butyl-phenyl)-2,3-dimethyl-2-propenyl]-piperidine.

144. A fungicidal composition, in accordance with claim 92, which contains 1-[3-(4-tert.butyl-cyclohexyl)-2-methyl-2-propenyl]-piperidine.

145. A fungicidal composition, in accordance with claim 92, which contains 1-[3-(4-tert.butyl-cyclohexyl)-2-methyl-2-propenyl]-3-methyl-piperidine.

146. A fungicidal composition, in accordance with claim 92, which contains 4-[3-(4-tert.butyl-cyclohexyl)-2-methyl-2-propenyl]-2,6-dimethyl-morpholine.

147. A fungidical composition, in accordance with claim 92, which contains 1-[3-(p-tert.butyl-phenyl)-2-methyl-propyl]-3,3-dimethyl-piperidine-1-oxide.

148. A fungicidal composition, in accordance with claim 92, which contains 4-[3-(4-tert.butyl-cyclohexyl)-2-methyl-propyl]-2,6-dimethyl-morpholine.

149. A fungicidal composition, in accordance with claim 92, which contains 1-[3-(4-tert.butyl-cyclohexyl)-2-methyl-propyl]-piperidine.

150. A fungicidal composition, in accordance with claim 92, which contains 1-[3-(4-tert.butyl-cyclohexyl)-2-methyl-propyl]-3-methyl-piperidine.

151. A fungicidal composition, in accordance with claim 92, which contains 4-[3-(p-tert.butyl-phenyl)-2-methyl-propyl]-2,6-dimethyl-morpholine-4-oxide.

152. A fungicidal composition, in accordance with claim 92, which contains 1-[3-(p-tert.butyl-phenyl)-2-methyl-propyl]-piperidine-1-oxide.

153. A fungicidal composition, in accordance with claim 92, which contains 1-[3-(p-tert.butyl-phenyl)-2-methyl-propyl]-3-methyl-piperidine-1-oxide.

154. A fungicidal composition, in accordance with claim 92, which contains 4-[3-(p-tert.butyl-phenyl)-2-methyl-propyl]-morpholine-4-oxide.

155. A fungicidal composition, in accordance with claim 92, which contains 1-[3-(p-tert.butyl-phenyl)-1,2,3-trimethyl-2-propenyl]-piperidine.

156. A fungicidal composition, in accordance with claim 92, which contains 1-[3-(p-tert.butyl-phenyl)-1,2,3-trimethyl-propyl]-piperidine.

157. A fungicidal composition, in accordance with claim 92, which contains 1-[3-(p-tert.butyl-phenyl)-1,2-dimethyl-2-propenyl]-piperidine.

158. A fungicidal composition, in accordance with claim 92, which contains 1-[3-(4-tert.butyl-cyclohexyl)-2-methyl-propyl]-3-ethyl-piperidine.

159. A fungicidal composition, in accordance with claim 92, which contains 1-[3-(4-tert.butyl-cyclohexyl)-2-methyl-propyl]-3,5-dimethyl-piperidine.

160. A fungicidal composition, in accordance with claim 92, which contains 1-[3-(4-tert.butyl-cyclohexyl)-2-methyl-propyl]-3,4-dimethyl-piperidine.

161. A fungicidal composition, in accordance with claim 92, which contains 1-[3-(4-tert.butyl-cyclohexyl)-2-methyl-propyl]-3-ethyl-4-methyl-piperidine.

162. A fungicidal composition, in accordance with claim 92, which contains 1-[3-(4-tert.butyl-cyclohexyl)-2-methyl-propyl]-3-ethyl-piperidine-1-oxide.

163. A fungicidal composition, in accordance with claim 92, which contains 1-[3-(4-tert.butyl-cyclohexyl)-2-methyl-propyl]-3,4-dimethyl-piperidine-1-oxide.

164. A fungicidal composition, in accordance with claim 92, which contains 1-[3-(4-tert.butyl-cyclohexyl)-2-methyl-propyl]-3,5-dimethyl-piperidine-1-oxide.

165. A fungicidal composition, in accordance with claim 92, which contains 4-[3-(4-tert.butyl-cyclohexyl)-2-methyl-propyl]-2,6-dimethyl-morpholine-4-oxide.

166. A fungicidal composition, in accordance with claim 92, which contains 1-[3-(4-tert.butyl-cyclohexyl)-2-methyl-propyl]-piperidine-1-oxide.

167. A fungicidal composition, in accordance with claim 92, which contains 1-[3-(p-tert.butyl-phenyl)-2-methyl-2-propenyl]-piperidine-1-oxide.

168. A fungicidal composition, in accordance with claim 92, which contains 1-[3-(4-tert.butyl-cyclohexyl)-2-methyl-2-propenyl]-3-methyl-piperidine-1-oxide.

169. A fungicidal composition, in accordance with claim 92, which contains 1-[3-(p-tert.butyl-phenyl)-2,3-dimethyl-2-propenyl]-3-methyl-piperidine.

170. A fungicidal composition, in accordance with claim 92, which contains 1-[3-(p-tert.butyl-phenyl)-2,3-dimethyl-2-propenyl]-3,5-dimethyl-piperidine.

171. A fungicidal composition, in accordance with claim 92, which contains 1-[3-(p-tert.butyl-phenyl)-2,3-dimethyl-propyl]-3-methyl-piperidine.

172. A fungicidal composition, in accordance with claim 92, which contains 1-[3-(p-tert.butyl-phenyl)-2,3-dimethyl-propyl]-3,5-dimethyl-piperidine.

173. A fungicidal composition, in accordance with claim 92, which contains 4-[3-(p-tert.butyl-phenyl)-2,3-dimethyl-propyl]-2,6-dimethyl-morpholine.

174. A compound of the formula

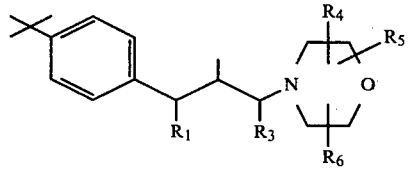

wherein $R_1$ and $R_3$, independently, are hydrogen or methyl;

$R_4$, $R_5$ and $R_6$, independently, are hydrogen or alkyl of 1 to 4 carbon atoms;

and the acid addition salts thereof.